(12) United States Patent
Penhasi

(10) Patent No.: US 9,757,276 B2
(45) Date of Patent: Sep. 12, 2017

(54) OCULAR IMPLANT WITH INTRAOCULAR FLUID PRESSURE REGULATION

(71) Applicant: OPR Group Ltd., Grand Cayman (KY)

(72) Inventor: Adel Penhasi, Holon (IL)

(73) Assignee: OPR GROUP LTD., Grand Cayman (KY)

( * ) Notice: Subject to any disclaimer, the term of this patent is extended or adjusted under 35 U.S.C. 154(b) by 71 days.

(21) Appl. No.: 14/357,570

(22) PCT Filed: Nov. 11, 2012

(86) PCT No.: PCT/IL2012/050450
§ 371 (c)(1),
(2) Date: May 11, 2014

(87) PCT Pub. No.: WO2013/069018
PCT Pub. Date: May 16, 2013

(65) Prior Publication Data
US 2014/0343476 A1    Nov. 20, 2014

Related U.S. Application Data

(60) Provisional application No. 61/558,471, filed on Nov. 11, 2011.

(51) Int. Cl.
*A61B 19/00* (2006.01)
*A61F 9/007* (2006.01)

(52) U.S. Cl.
CPC .. *A61F 9/00781* (2013.01); *A61F 2230/0067* (2013.01); *A61F 2250/0018* (2013.01); *A61F 2250/0031* (2013.01); *A61F 2250/0036* (2013.01)

(58) Field of Classification Search
CPC .................................................. A61F 9/00781
USPC ........................................................ 604/8, 9
See application file for complete search history.

(56) References Cited

U.S. PATENT DOCUMENTS

2004/0254517 A1* 12/2004 Quiroz-Mercado ............. A61F 9/00781
604/8

FOREIGN PATENT DOCUMENTS

WO    WO 2009012406 A1 *   1/2009   ......... A61F 9/00781

* cited by examiner

*Primary Examiner* — Leslie Deak
(74) *Attorney, Agent, or Firm* — Graeser Associates International Inc; Dvorah Graeser

(57) ABSTRACT

An ocular implant comprising a shunt and a fluid absorbing conduit for reducing intraocular pressure, and optionally comprising a biodegradable ring.

21 Claims, 17 Drawing Sheets

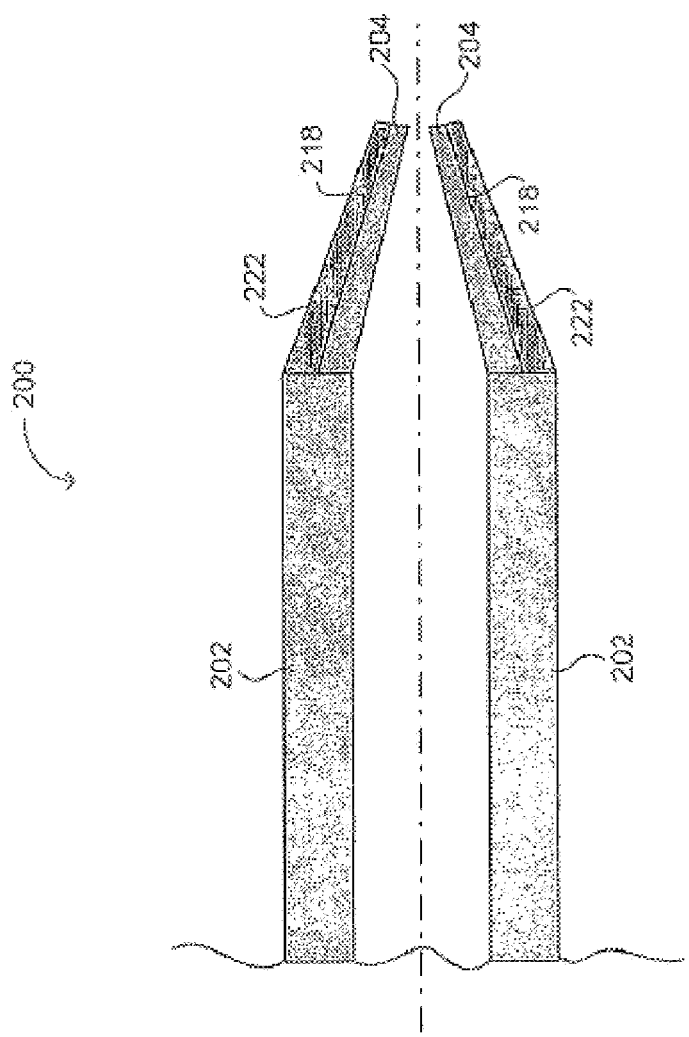

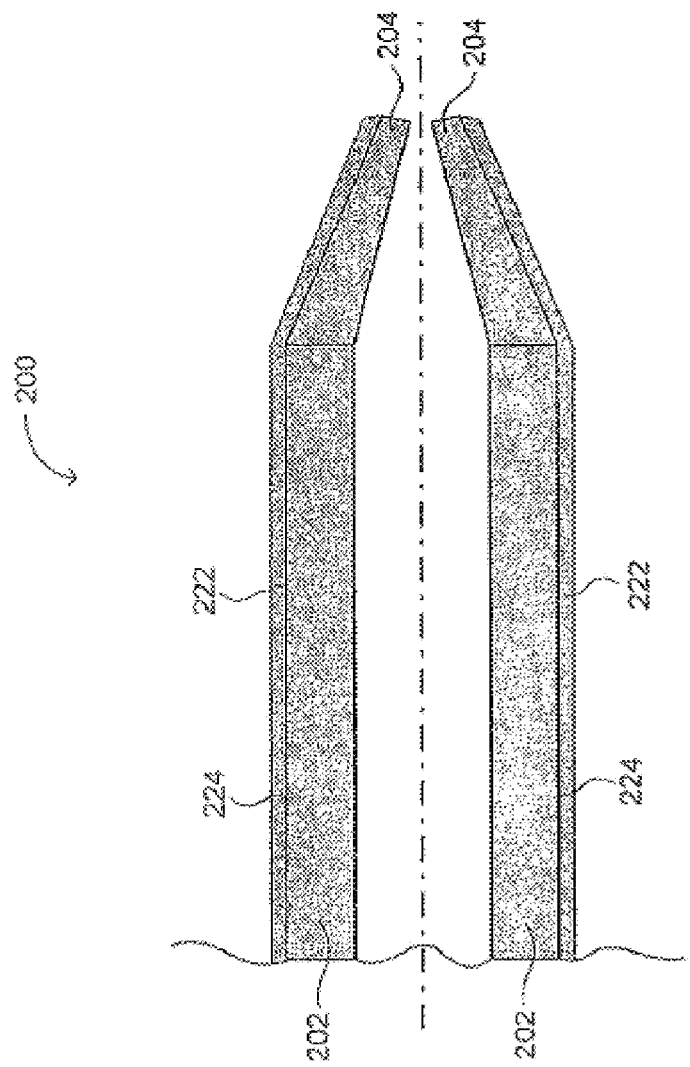

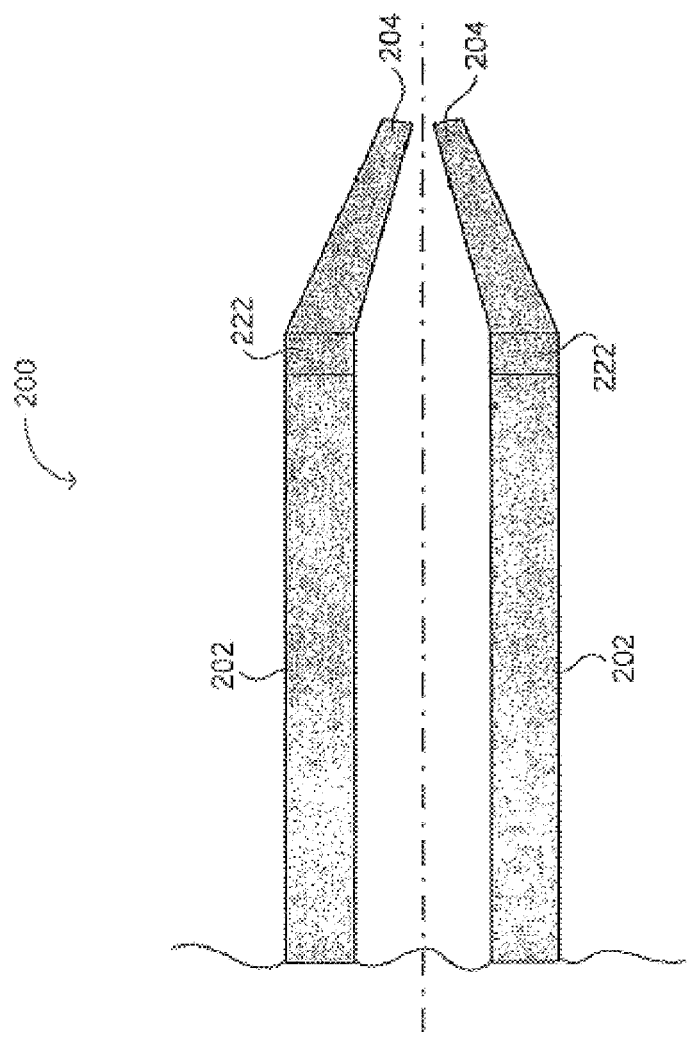

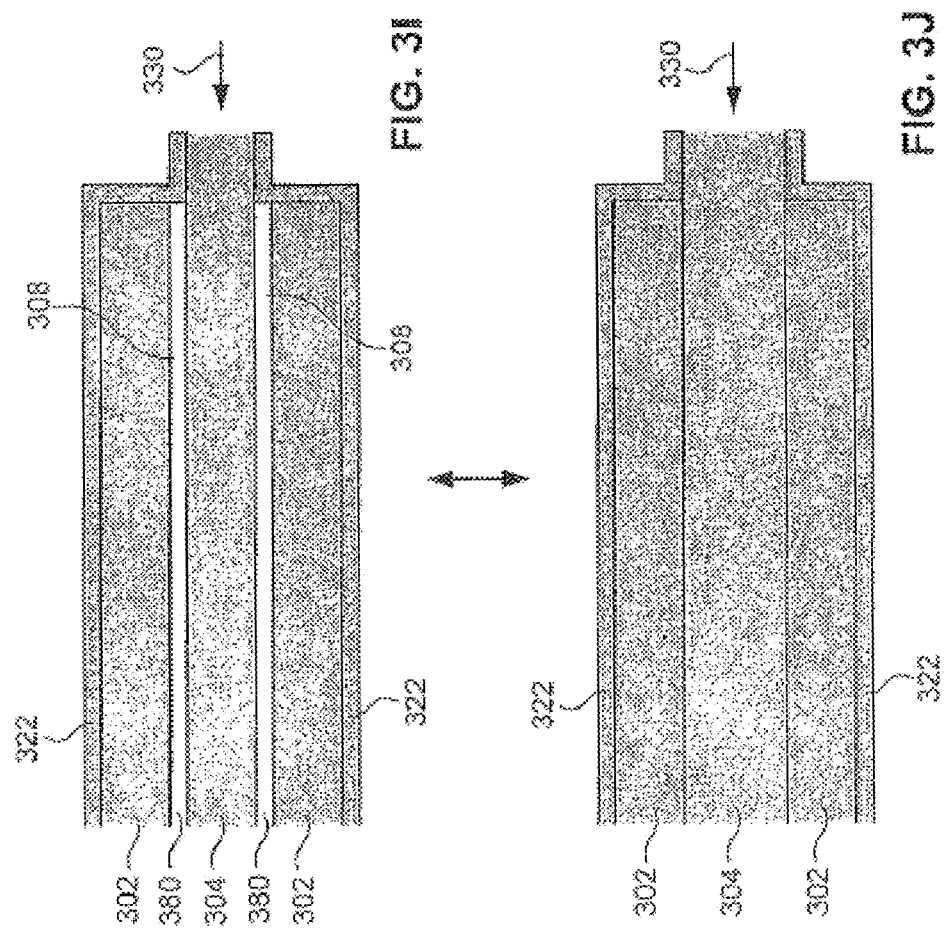

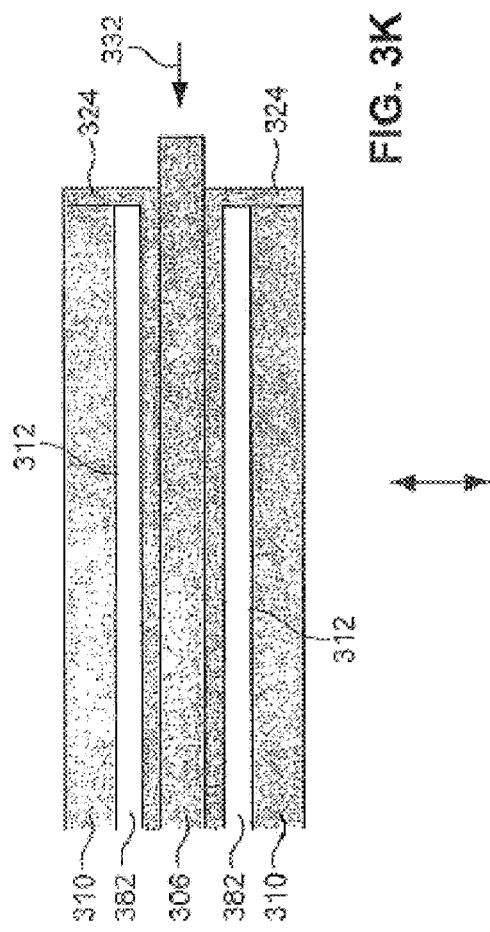
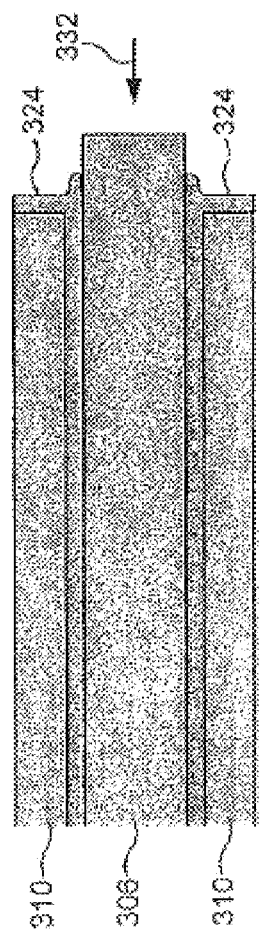

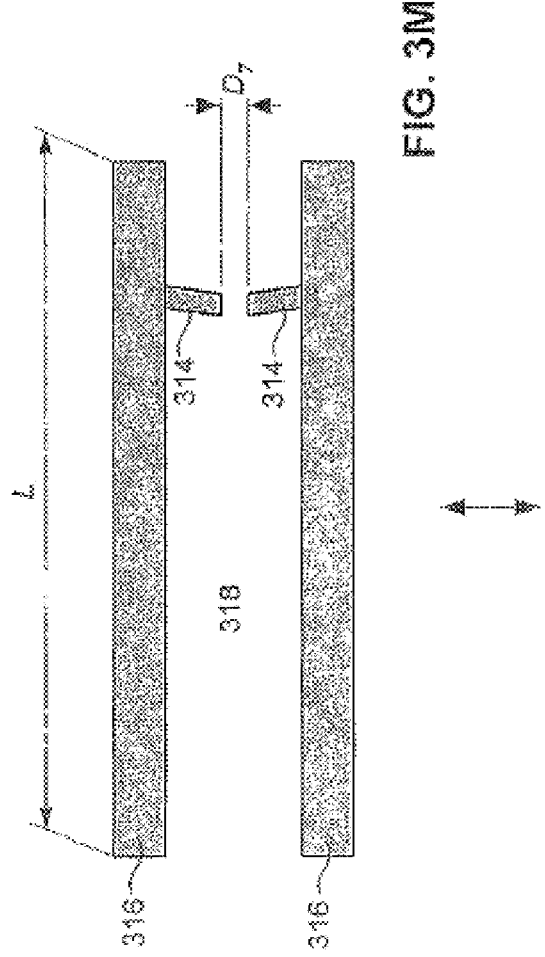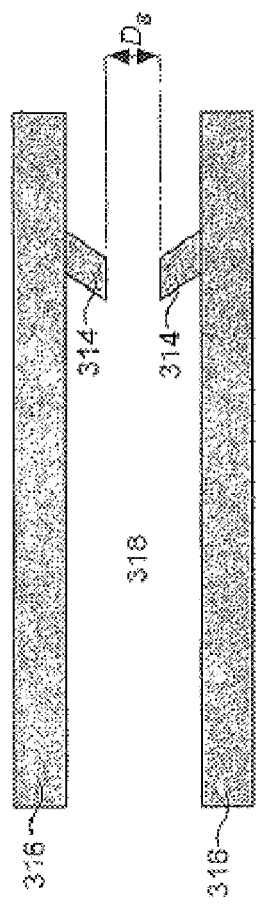
FIG. 3M
FIG. 3N

OCULAR IMPLANT WITH INTRAOCULAR FLUID PRESSURE REGULATION

FIELD OF THE INVENTION

The invention described herein relates to medical devices, in general, and to ocular implants, in particular.

BACKGROUND OF THE INVENTION

Glaucoma refers to a group of diseases that can damage the optic nerve of the eye and consequently may cause blindness or visual impairment. Glaucoma is one of the major causes of blindness and one of the leading causes of preventable blindness. Typically, glaucoma is characterized by noticeable changes in the optic nerve, sometimes associated with high or elevated intraocular pressure (TOP) and loss of peripheral vision. TOP above the normal physiological range (i.e., typically greater than 21 mmHg), may optionally be a sign of improper drainage of intraocular fluid (e.g., aqueous humor), which is normally produced at a rate of 2.5 ml/minute (i.e., this production rate typically varies among individuals). A rise in intraocular pressure, subjects the optic nerve to a pressure, referred to as the cupping of the optic disc. This condition is called glaucoma. Glaucoma does not usually cause pain, does not affect the central vision, and it is not detected by the patient, at least at an early stage, when proper treatment may optionally be prescribed, to prevent progress to an advanced stage.

Research indicates that possible causes of glaucoma may be an excessive release of pigmentation, a build up of proteins or other chemicals, the flaking of the iris or other tissues (e.g., ciliary bodies) and the like. These conditions, such as the excessive release of pigmentation lead to blockage of the trabecular meshwork, thereby preventing proper drainage of the aqueous humor from the eye. When the blockage is severe, aqueous humor accumulates in the anterior and posterior chamber, thereby increasing IOP. High IOP reduces blood flow to the eye and increases the hydraulic pressure on the optic nerve. The increased pressure may progressively interrupt the metabolic processes of cells in the optic nerve and consequently lead to a progressive destruction of the optic nerve. The outcome is permanent damage to the optic nerve, which causes degeneration of vision and eventually, to complete loss of vision.

SUMMARY OF THE INVENTION

It is an object of the present invention to provide a novel ocular implant for regulating intraocular fluid pressure of intraocular fluid that is contained within an anterior chamber of an eye of an implantee, who is implanted with the ocular implant.

According to some demonstrative embodiments, there is provided an ocular implant comprising a shunt and at least one fluid absorbing conduit.

According to some embodiments, the shunt may include at least one inlet, and at least one outlet that define at least one respective shunt conduit therebetween.

According to some embodiments, the at least one outlet may communicate with a space that is external to the anterior chamber of the eye.

According to some embodiments, the at least one fluid absorbing conduit may be coupled with at least one of the inlets. The fluid absorbing conduit may be composed from a material having a property of expanding when absorbing intraocular fluid, and contracting when desorbing from the intraocular fluid.

In some embodiments, the fluid absorbing conduit may include at least one port.

According to some embodiments, the at least one fluid absorbing conduit may be coupled with the shunt and communicating with the intraocular fluid.

According to some demonstrative embodiments, the port may increase, for example, when the absorption of the intraocular fluid by the fluid absorbing conduit increases, and may decrease, for example, when desorption of the intraocular fluid by the fluid absorbing conduit increases.

BRIEF DESCRIPTION OF THE DRAWINGS

The invention described herein in accordance with some demonstrative embodiments will be understood and appreciated more fully from the following detailed description taken in conjunction with the drawings in which:

FIG. 2A is a partial schematic cross-sectional illustration of an ocular implant, constructed and operative in accordance with another embodiment of the disclosed invention;

FIG. 2B is a partial schematic cross-sectional illustration showing another configuration of the ocular implant of FIG. 2A;

FIG. 2D is a partial schematic cross-sectional illustration showing another configuration of the ocular implant of FIG. 2A;

DETAILED DESCRIPTION OF THE INVENTION

Figure 1A:
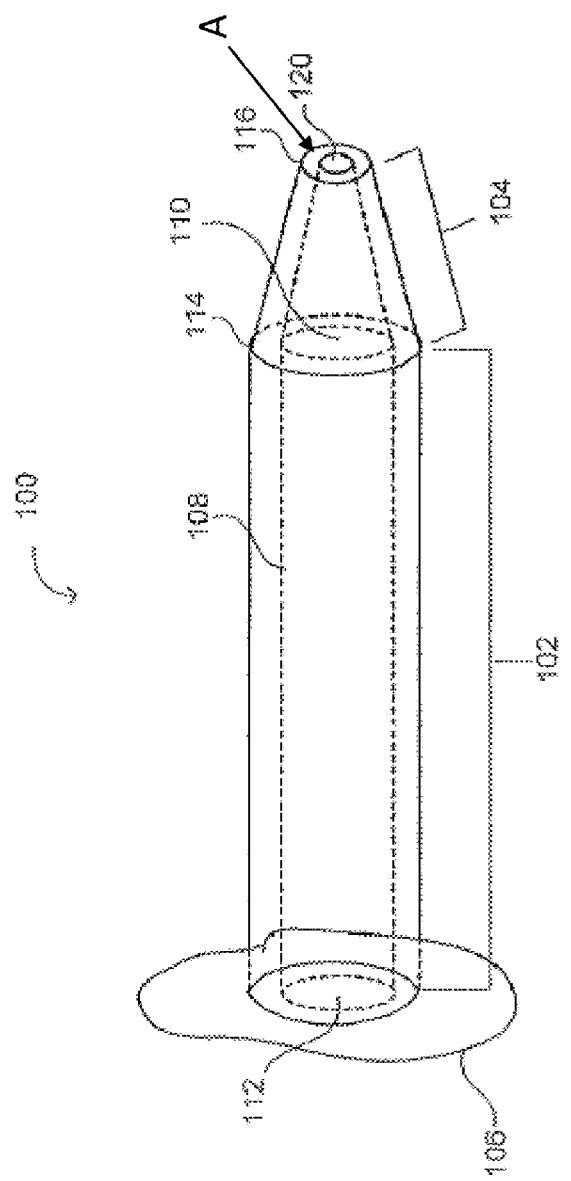
FIG. 1A is a schematic illustration of an ocular implant, constructed and operative in accordance with an embodiment of the disclosed invention.

In a normally functioning eye, aqueous humor, produced by the ciliary body, nourishes the anterior portion of the eye.

The aqueous humor is primarily drained through the trabecular meshwork into Schlemm's canal and finally enters the bloodstream. In open angle glaucoma (OAG), for example, the drainage passageway connecting the trabecular meshwork and Schlemm's canal is clogged, thereby increasing IOP in the anterior chamber. At its onset, open-angle glaucoma usually exhibits no perceivable symptoms.

Another type of glaucoma is angle-closure glaucoma (ACG). In contrast to OAG, ACG occurs when the iris moves over the trabecular meshwork in the anterior portion of the eye, thereby effectively narrowing the approximate 45° angle existing between the iris and the cornea. As the angle between the iris and the cornea narrows, the outflow of aqueous humor diminishes, thereby increasing the IOP. Furthermore, patients with ACG tend to have smaller anterior chambers, which can further exacerbate the condition. As with OAG, when the IOP rises, the patient is at an increased risk of damage to the optic nerve, which may lead to irreversible loss of vision.

Glaucoma patients can generally be treated by medication, laser intervention, surgical procedures, and by drug therapy. Drug therapy, however, may be problematic due to lack of compliance on the part of the patients. Moreover, side effects, associated with drugs, in general, may not be tolerable or acceptable by the patient. Furthermore, there are situations where surgical intervention may be more economically feasible than the usage of medicines for extended periods of time. In cases where medical or laser treatment (e.g., argon laser trabeculoplasty) is inadequate to lower the IOP, surgical procedures may represent the last resort to prevent complete loss of vision.

Trabeculectomy is a filtration surgery, which uses conventional surgical techniques, and involves opening of a passage (e.g., via an incision) in the sclera for draining of the aqueous fluid. A small bubble, called a bleb, forms over the opening, indicating that the aqueous fluid is draining. A procedure called bleb needling may sometimes restore drainage of fluid by allowing the opening of the scarred area. Drugs which destroy fibroblasts (i.e., connective tissue cells) may be employed. However, these drugs may bring about serious complications, such as infections. Other types of complications due to filtration surgery include cataracts, hypotony, bleb leaks, endophthalmitis and the like.

Another method for treating glaucoma is based on non penetrating surgery. In non penetrating surgery entry into the anterior chamber is avoided, thereby reducing the risk of intraoperative and postoperative hypotony (i.e., excessively low levels of IOP) from occurring by the use of this method. Furthermore, non penetrating surgery can significantly lower the chances of postoperative anterior chamber inflammation. Non-penetrating surgery may also significantly lower the risk of bleb-related endophthalmitis (BRE). Other methods for treating glaucoma include deep sclerectomy and viscocanalostomy. It is noted that some cases might further require postoperative laser treatment at the surgical site, when filtration is insufficient. Different complications are associated with non penetrating surgery, such as when steroids are administered, thereby leading to postoperative rise of IOP, large cystic blebs, and hyphema.

Non-penetrating deep sclerectomy (NPDS), known as non penetrating trabeculectomy, is an operation that attempts to induce drainage of intraocular fluid without entering the anterior chamber of the eye. This technique involves creation of a limbus based conjunctival flap (i.e., a drainage pathway). The natural healing response of the body for closure of the drainage pathway, however, has led to a high failure rate. In order to prevent inevitable late stage fibrosis that may result, different types of implants such as SK-Gel (a cross-linked hyaluronic acid, manufactured by Corneal in France), and AquaFlow (a collagen manufactured by STAAR Surgical Co. of Monrovia, Calif.), which biodegrades in six to nine months, have been employed with varying degrees of success. The main goal of these implants is to hold the drainage pathway open long enough during the healing process, in order to drain excess accumulated aqueous fluid.

Another known surgical procedure for treating glaucoma is viscocanalostomy. In a viscocanalostomy procedure, the surgeon creates two scleral flaps. After Schlemm's canal has been opened, the surgeon inserts a cannula into Schlemm's canal, and after tightly closing the superficial flap, the surgeon injects a high viscosity viscoelastic fluid (e.g., Healon, Sodium Hyaluronate, Pharmacia) underneath the scleral flap to create a reservoir.

Generally, glaucoma drainage implants are employed to enhance standard glaucoma filtration surgery by positioning a device that allows the preservation of the surgically created drainage open. If this drainage is not maintained open, it will eventually become blocked due to the natural healing process of the body. Generally, whatever the type of the implant, the goal is to decrease TOP by increasing outflow of aqueous fluid from the eye. Glaucoma implants may be considered in cases of glaucoma due to injury to the eye. Glaucoma implants are also used in cases of congenital glaucoma, neovascular glaucoma (i.e., a type of glaucoma often associated with diabetes), and in cases where other types of surgeries have failed.

Modern glaucoma implants generally conform to a common design. These implants generally include a long silicon rubber tube attached at one end to a synthetic plate or a band of variable shape and surface area. The tube is inserted into the anterior or posterior chamber of the eye through a scleral fistula at the level of the limbus or pars plana. The synthetic plate or the band, is sutured at an episcleral surface, posterior to insertion of the rectus muscles (i.e., under the upper eyelid). Following implantation, the reservoir plate or the band undergo capsulation by the tissues of the eye, which form a fibrous capsule that surrounds the reservoir plate or the band. The fibrous capsule serves as a sub conjunctival reservoir into which the aqueous humor is shunted via the silicon rubber. The capillaries and part of the lymphatic system, existing in the envelope, reabsorb the aqueous fluid into the blood vessels and tissues around it. The inherent resistance of the capsular wall (i.e., surrounding the reservoir plate), to passive transmural fluid diffusion, as well as the total capsular surface area (i.e., the surface area of the fibrous capsule formed around the reservoir plate) are responsible for achieving a steady state TOP (i.e., by controlling the diffusion rate of aqueous humor drainage).

Since glaucoma implants are considered foreign bodies when they are implanted in an implantee, an immunoreactive effect may result, thereby causing inflammation at the site of the surgery. The use of a glaucoma drainage implant is commonly associated with a rise in TOP, which usually stabilizes in four to six weeks. The success of implantations and the length of time in which they are effective, appear to be related to the surface area (i.e., of the reservoir plate), which is covered by the implant for drainage. The larger the implant surface area, the greater the chances of success. Certain tradeoffs, however, are associated with implant therapy. The greater the size of the implant, the greater the chance that complications might occur. One condition that can result in the early post operative period of implantation, due to excessive drainage is hypotony (i.e., typically, TOP less than a safe minimum level of 5 mmHg). The TOP should ideally remain within a safe range (i.e., of 5 to 15 mmHg) after implantation of the glaucoma drainage implant, in order to prevent both early hypotony and later inadequate drainage.

Glaucoma implants are often used when other surgeries have failed due to the natural healing process of the body, which causes scarring over the surgical opening. In these cases, IOP returns to higher pre-surgical levels. Glaucoma implants may be associated with other similar complications. The narrow opening in the tube of an implant, located in the front part of the eye may become clogged. Excessive scarring around the external drainage portion of the implant might block the re absorption of the aqueous fluid, thereby leading to inadequate IOP control. Other complications may include corneal injury, which can result from mechanical friction between the tube or reservoir and the tissues of the eye. Corneal injuries may require surgical operation and sometimes the removal of the glaucoma implant.

Examples of basic implant design, developed by Molteno, and by Krupin, are known in the art Implants such as Baerveldt by Advanced Medical Optics, Inc. (AMO), Molteno by Molteno Ophthalmic Ltd, Krupin, Schocket, Ahmed, Josef, White, OptiMed by Optimed Inc., Ex-PRESS by Optanol Ltd, and Eyepass by GMP Companies Inc. have been introduced with modifications designed to enhance IOP control, and to reduce early postoperative complications. The implants commonly used, differ primarily on the basis of existence of a pressure-sensitive valve, the shape and surface area of the scleral explant, and whether the implant is dedicated for deep sclerectomy (i.e., via bypass).

As mentioned above, one of the complications associated with glaucoma drainage implants is hypotony, resulting from excess drainage of aqueous humor in the early postoperative period, prior to fibrous encapsulation of the scleral plate (i.e., prior to bleb formation). In order to prevent hypotony, it is necessary to restrict the flow of the aqueous fluid through the tube of the implant. For this purpose a new generation of glaucoma implants, termed valved glaucoma implants, have been designed and manufactured. When a drainage device with a non valved drainage tube is employed, the aqueous fluid flow is generally restricted by using one of a variety of suture ligatures with or without a releasable stent (i.e., such a device temporarily prevents outflow of aqueous fluid). Profound hypotony will generally result if there is nothing to restrict the outflow of aqueous during the initial one to two weeks following the operation.

Valved glaucoma drainage implants, in which the tube has been modified to provide some restriction to aqueous fluid flow (e.g., Ahmed Glaucoma Valve, Krupin Eye Disk), may overcome the problem of early postoperative hypotony. The need for ligatures or stents, in these implants, at the time of surgery, is eliminated by employing a valve mechanism, which is designed to maintain the TOP within a specific physiologic range (i.e., approximately 8 to 12 mmHg).

Valved drainage devices may also provide an added margin of safety for an extended period of time, beyond the immediate postoperative period, in case of abnormal ciliary body function. In cases where there are low levels of aqueous secretion, which may occur with severe ocular ischemia and chronic or recurrent uveitis, IOP should be kept above the stated closing pressure of the valve, in order to avoid hypotony.

Some studies show, however, that the valves in these devices behave more like flow restrictors than actual true valves. The ability of these devices to consistently maintain the TOP within strictly defined ranges is usually unreliable.

It is crucial to avoid both excessively high levels of TOP (i.e., which might occur with the use of a non-valved, ligatured tubes) and hypotony (i.e., excessively low levels of IOP), and its attendant complications (i.e., that might result from a non-ligatured tubes, non-valved tubes). It is noted that ligatured tubes are implants through which the flow of aqueous is temporarily restricted, typically using an absorbable suture (during the first period post implantation). High intraocular pressures, caused by an obstructed valve may be problematic as well. It is noted that fibrous capping of the distal portion of implanted tubes, in the vicinity of the valve, may occasionally occur. Furthermore, difficulties associated with valved drainage devices and the unpredictable functions of the valve mechanisms restrict their usefulness. In eyes, which are associated with a high risk of postoperative complications (e.g., aphakic, vitrectomized, multiple prior intraocular surgeries), use of other treatment routes, rather than using a valved glaucoma implant, should be considered.

Drainage as a result of flow-restriction modifications provides immediate IOP reduction and further eliminates the need for temporary tube ligatures or stents. Thus, it reduces operation time and eliminates the need of a consequent operation to release a ligature, or remove a stent. Furthermore, in situations where preoperative IOP is extremely elevated after all possible medication treatments have been administered, or where aqueous fluid hyposecretion is anticipated postoperatively, use of a drainage device containing a pressure-sensitive valve should be considered.

US Patent Application Publication No. 2007/0293872 A1 to Peyman entitled "Ocular draining device" is directed to a device and to a method of using the device for draining aqueous and vitreous fluid from the eye after glaucoma surgery. The device includes a shunt, a collapsible conduit, a stylet and a reservoir. The shunt has a proximal end and a distal end, defining a lumen therein. The collapsible conduit is tubular, includes detents, and possesses a proximal end and a distal end that define a lumen therein. The stylet has a proximal end and a distal end and includes a sharp tip at the distal end. The reservoir is formed of a mesh material, and includes a locking mechanism. The reservoir is connected to the proximal end of the shunt via the locking mechanism. The collapsible conduit surrounds the shunt. The shunt is in fluid communication between the anterior chamber and the exterior of the eye.

The stylet passes inside the shunt and its sharp tip penetrates the eye in order to implant the shunt and collapsible conduit within the eye. The stylet is removed after the distal end of the shunt and the collapsible conduit are placed inside the anterior chamber. The detents apply pressure to the outer surface of the shunt when the collapsible conduit deforms under pressure. The shunt is formed of a radially expandable mesh material, which may optionally be axially compressed by the movement of the detents owing to the pressure. Thus, the lumen reduces or closes the shunt, thereby controlling the flow rate of fluid out of the eye. The conduit is formed of a resilient material and regains its original shape after external pressure is removed or the internal fluid pressure diminishes. Fluid drains from the interior chamber through the shunt and into the reservoir when the stylet is removed.

U.S. Pat. No. 5,713,844 issued to Peyman and entitled "Device and method for regulating intraocular pressure" is directed to a device and to a method for regulating intraocular pressure within the anterior chamber of an eye of a patient. The device includes an interior tube, an exterior tube and a reservoir. The interior tube includes one terminus that is open, another terminus that is attached to the reservoir, and a weak spot in its wall. The exterior tube is flexible and forms a closed chamber around the length of the interior tube, but does not occlude the termini of the interior tube. The interior tube is composed of a semi-flexible polymer, and exterior tube is composed of a semi-solid polymer.

After implantation of the device in the eye, the open terminus of the interior tube opens into the anterior chamber. Aqueous fluid in the anterior chamber enters the open terminus and flows to the reservoir via the internal tube. Intraocular pressure of the patient is routinely monitored. When low intraocular pressure is detected, an exogenous fluid is added to the exterior tube, thereby exerting pressure on the interior tube. This pressure deforms the interior tube at the weak spot, thereby reducing the diameter of the interior tube, and therefore reducing or obstructing the flow of aqueous fluid through the interior tube.

U.S. Pat. No. 6,544,208 issued to Ethier et al. and entitled "Implantable shunt device" is directed to an implantable shunt device for controlling internal pressure. The implantable shunt device includes a valve assembly, a suture plate and an inlet tube. The valve assembly includes valve housing, an inflow port, an outflow port, an osmotic pressure chamber, a collapsible flexible tube, and a membrane assembly. The membrane assembly includes a semi-permeable membrane. The semi permeable membrane has an inner surface and an outer surface. The collapsible flexible tube includes a highly flexible tube that completely collapses under external pressure. The outer surface of the semi permeable membrane is in communication with bodily fluids, and the inner surface thereof is in communication with the interior of the osmotic pressure chamber. The ends of the collapsible tube are connected to the inflow port and the outflow port. The suture plate is attached to the valve housing.

The implantable shunt device is implanted by suturing to a scleral surface of the eye. The inlet tube is inserted into the anterior chamber of the eye. The osmotic pressure chamber is filled with a solution that generates an osmotic pressure. Osmotic pressure obtained after the implantable shunt device is implanted may optionally be altered by changing the concentration of the solute in the osmotic pressure chamber. Fluid flows from the anterior chamber through the inlet tube to the collapsible flexible tube and then exits the device. The fluid pools around the implantable shunt device, thereby forming a bleb. Fluid from the bleb filters through the semi-permeable membrane into the osmotic pressure chamber. When pressure inside the collapsible tube exceeds a certain value, the collapsible flexible tube opens and allows fluid passage, or else, the collapsible flexible tube is collapsed thereby preventing the passage of fluid.

US Patent Application Publication No. 2005/0277864 to Haffner et al., entitled "Injectable gel implant for glaucoma treatment" is directed to a method and implant devices for treating glaucoma. The implant device is a seton implant, and is functional as a trabecular stent. The seton implant includes an inlet end, an outlet end, and a lumen therebetween. The inlet end is positioned in an anterior chamber of an eye, and the outlet end is positioned at an exterior surface of the trabecular meshwork of the eye of a patient. The seton implant is comprised of a biocompatible material, such as a hydrogel. The seton implant permits flow of aqueous from an anterior chamber to Schlemm's canal of the eye.

The implant device as a trabecular stent includes a distal opening and a proximal opening. The distal opening is disposed in Schlemm's canal and the proximal opening is disposed in the anterior chamber, thereby bypassing the trabecular meshwork. Injectable foam material is inserted through the trabelcular stent and fills a portion of Schlemm's canal. The injectable foam material may optionally be created by superporous hydrogel. The injectable foam material is injected via a syringe type injector that penetrates the trabecular meshwork. The injected foam material expands as the foam sets and absorbs aqueous.

US Patent Application Publication No. 2005/0119737 A1 to Bene et al. and entitled "Ocular implant and methods for making and using same" is directed to an ocular implant device that is insertable into either the anterior or posterior chamber of the eye to drain aqueous humor and/or to introduce medication. The ocular implant device, termed "shunt", includes an opening, a solid member, a distal end comprising a head, a proximal end comprising a foot, and a body extending between the head and the foot. The opening, which includes a wider portion and a narrowed portion, extends between the distal end and the proximal end. The solid member includes a flap, which opens only in one direction. The wider portion includes a filter. The flap is constructed of a hydrogel material. The distal end deforms upon hydration allowing easier implantation. The solid member covers the narrowed portion and maintains the flap in a closed position until a minimal pressure is applied from the distal direction of the opening. The flap opens to allow flow from the distal to the proximal end of the opening.

The shunt may further include a cap, which covers the opening. The cap is constructed of porous hydrogel membrane in order to control the flow of fluid, via controlled diffusion, between the distal end and the proximal end of the opening.

US Patent Application Publication No. 2004/0127843 to Tu et al., entitled "Glaucoma implant with therapeutic agents" is directed to implant devices and methods for the treatment of glaucoma. The implant devices include a seton implant, which includes a one way controlling means, and an elongated tubular element having a distal section and an inlet section. The distal section is positioned inside an outflow pathway in an eye of a patient. The distal section includes a radially protruding retention device.

The seton implant is made of a biocompatible material such as a hydrogel. The seton implant facilitates the outflow of aqueous into Schlemm's canal in order to balance intraocular pressure. After implantation, the retention device stabilizes the seton implant inside the outflow pathway. The one way flow controlling means allows the flow of aqueous in one way from the inlet section to the distal section. The use of a biocompatible material that hydrates and expands after implantation locks the seton implant into position around the trabecular meshwork in the eye.

The disclosed invention overcomes the disadvantages of the prior art by providing an ocular implant for regulating intraocular fluid pressure contained within an anterior chamber of the eye, having a shunt and a fluid absorbing conduit coupled with the shunt.

According to some embodiments, the fluid absorbing conduit may have a port that may be in fluid communication with the intraocular fluid in the anterior chamber. Optionally, the fluid absorbing conduit may be composed from a material having the property of expanding when absorbing intraocular fluid and contracting when desorbing from intraocular fluid.

For example, when intraocular pressure within the anterior chamber of the eye increases, the fluid absorbing conduit may absorb more intraocular fluid thereby expanding, and the port dilates to allow intraocular fluid to drain. When intraocular pressure within the anterior chamber of the eye decreases, the fluid absorbing conduit may absorb less intraocular fluid (i.e., at least partially desorbs therefrom), thereby contracting, and the port may constrict to limit the outflow of the intraocular fluid from the anterior chamber.

The terms "implantee", and "patient", are herein used interchangeably and may refer to a human being and/or an animal, to whom an ocular implant is directed. The term "implant" as used herein, refers to a substance or object (e.g., a manufactured device), for example, for introducing into a tissue of a patient. The terms "aqueous humor", "aqueous", and "intraocular fluid" are used herein interchangeably and may refer to the transparent, gelatinous fluid that is generally secreted from the ciliary epithelium of the eye. The terms "degradation" and "biodegradation" are used herein interchangeably and refer to the conversion, the decomposition, or the break down of substances by living organisms (e.g., bacteria, fungi), by enzymes, acids, bases, salts, and the like.

Figure 1B:
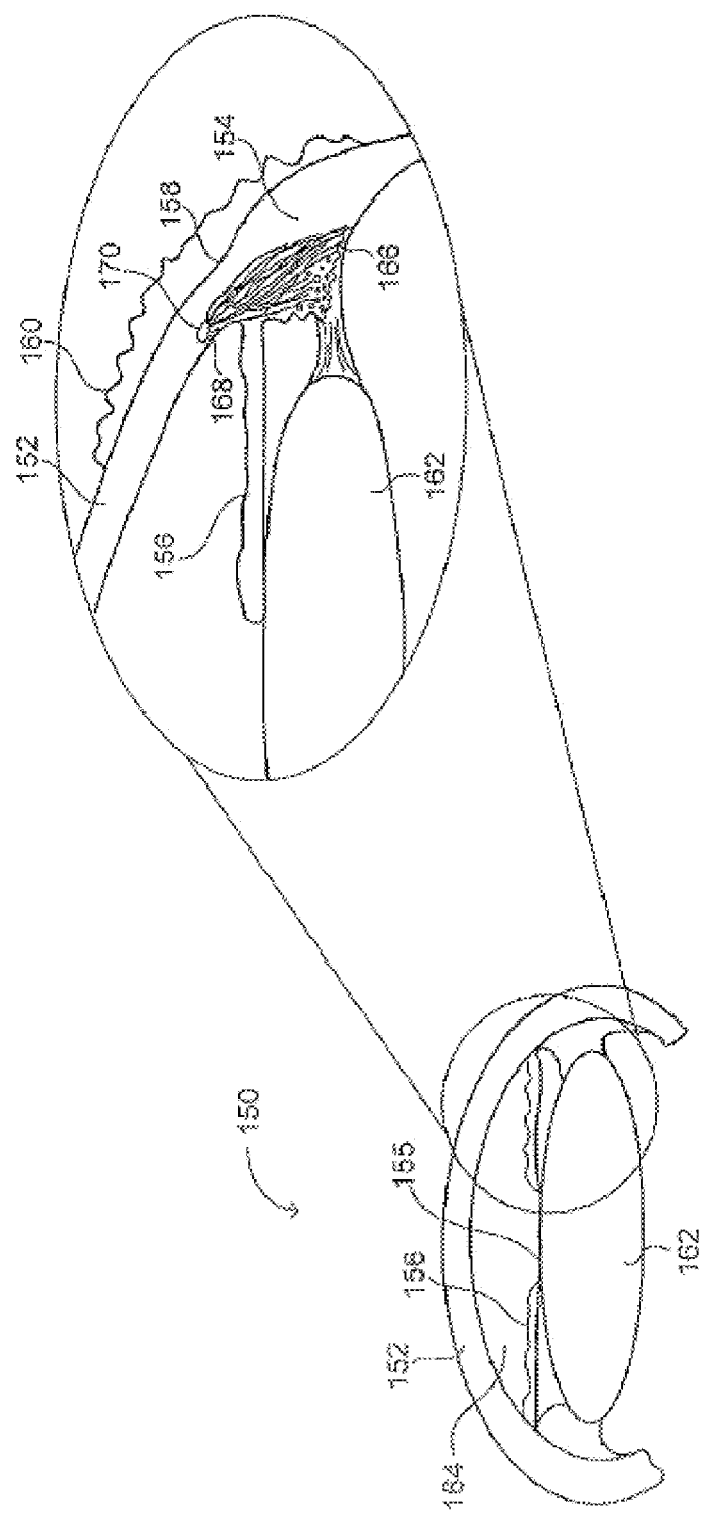
FIG. 1B is a schematic illustration of a partially representative cross-sectional view of the anatomy of an eye.
Figure 1C:
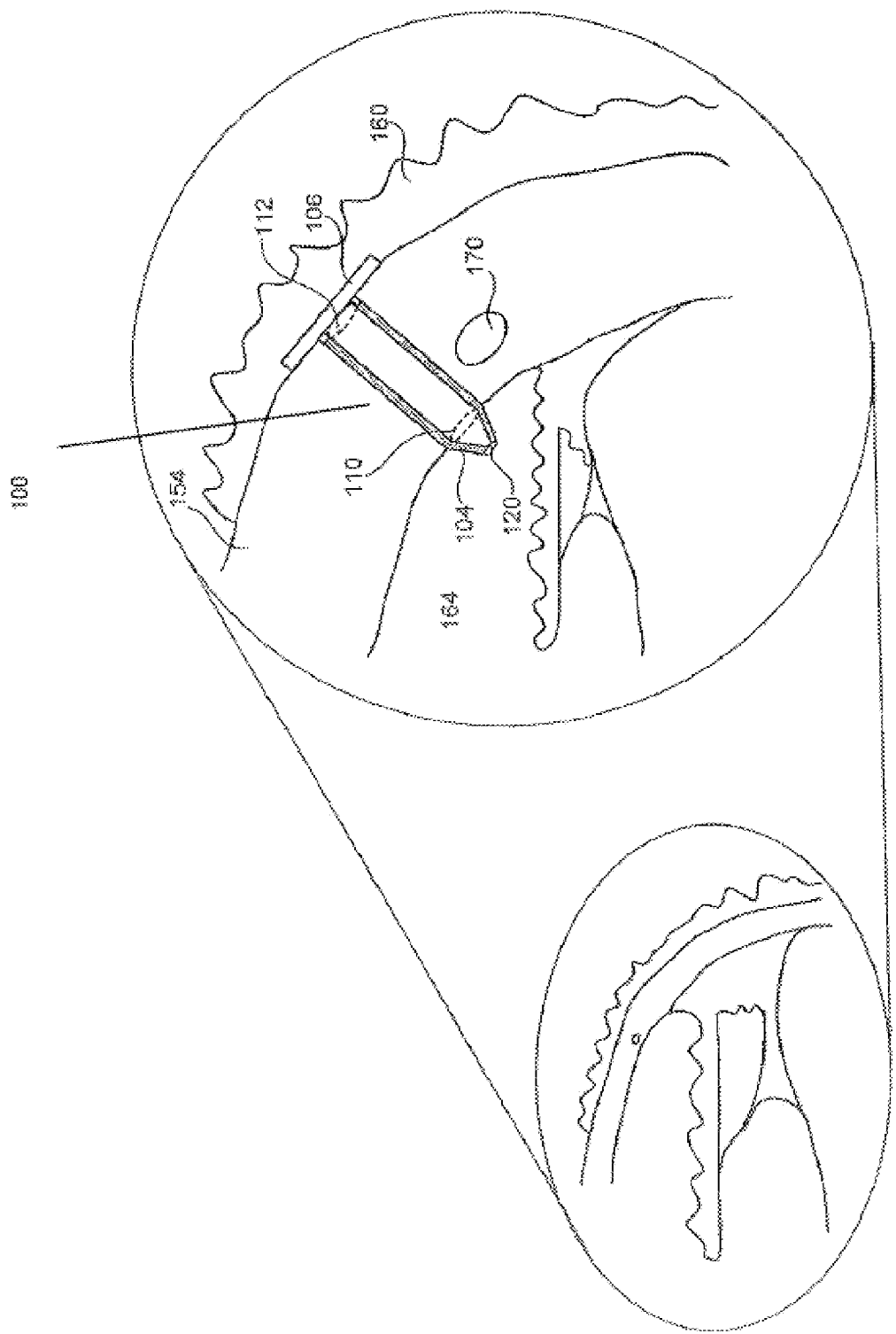
FIG. 1C is a schematic illustration of the ocular implant of FIG. 1A implanted into an eye of an implantee.
Figure 1D:
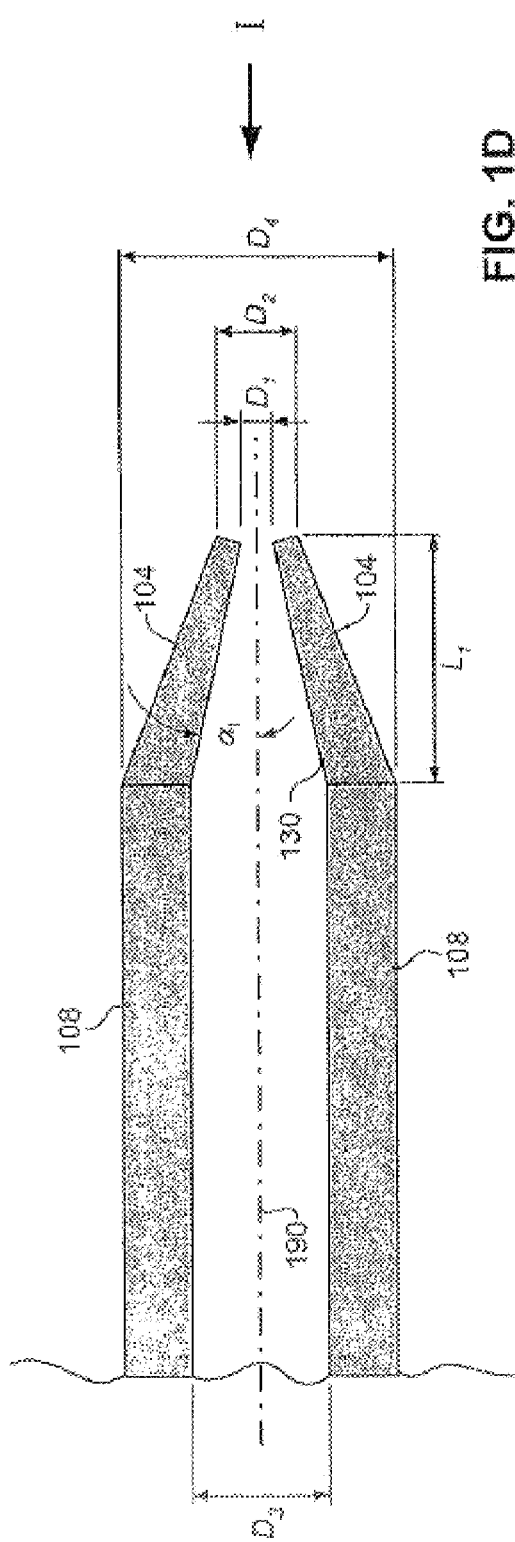
FIG. 1D is a partial schematic cross-sectional illustration of the ocular implant of FIG. 1A, being in a particular representative operative state.
Figure 1E:
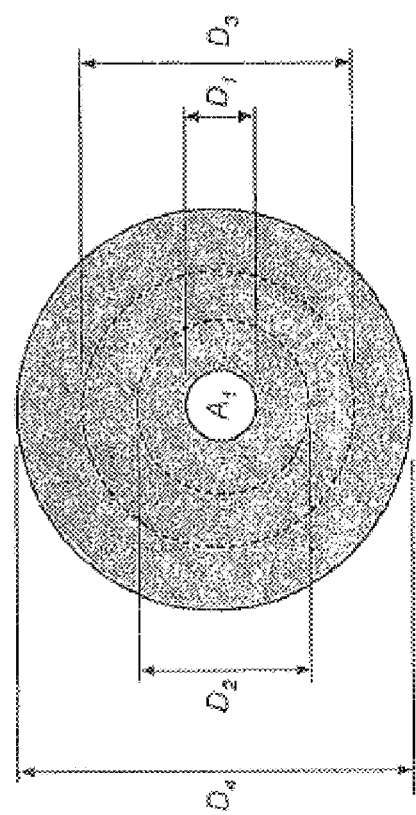
FIG. 1E is a schematic cross-sectional illustration taken along a longitudinal axis in a direction of I of FIG. 1D.
Figure 1F:
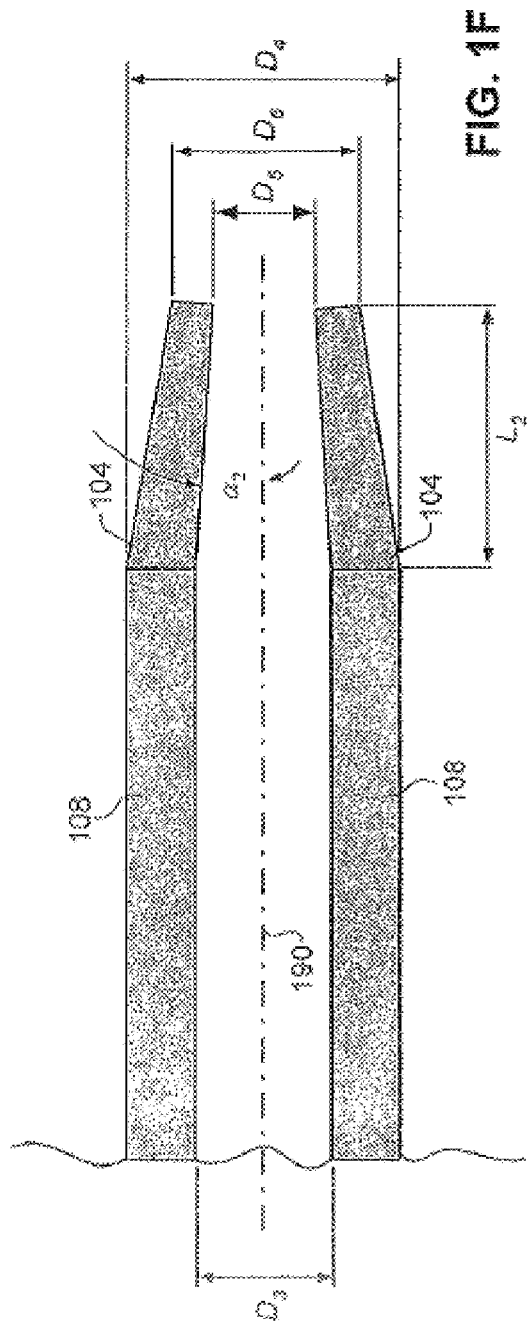
FIG. 1F is a partial schematic cross-sectional illustration of the ocular implant of FIG. 1A, being in another representative operative state.
Figure 1G:
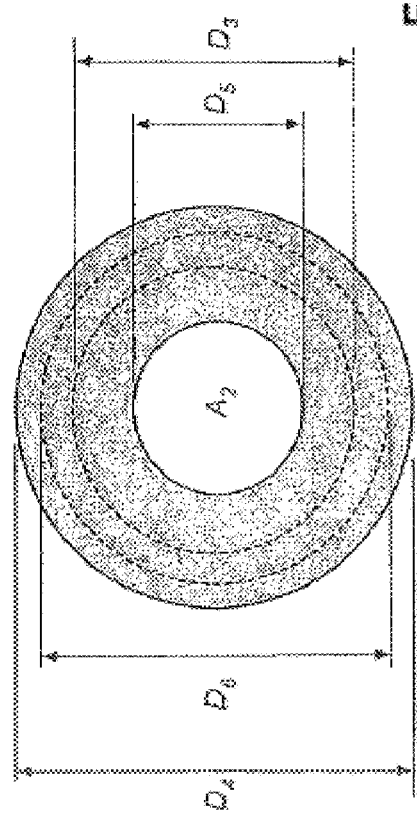
FIG. 1G is a schematic cross-sectional illustration taken along a longitudinal axis in the direction of II of FIG. 1F.

Reference is now made to FIGS. 1A, 1B, 1C, 1D, 1E, 1F, and 1G. FIG. 1A is a schematic illustration of an ocular implant, generally referenced 100, constructed and operative in accordance with an embodiment of the present invention. FIG. 1B is a schematic illustration of a partially representative cross-sectional view of the anatomy of an eye. FIG. 1C is a schematic illustration of the ocular implant of FIG. 1A implanted into an eye of an implantee. FIG. 1D is a partial schematic cross-sectional illustration of the ocular implant of FIG. 1A, being in a particular representative operative state. FIG. 1E is a schematic cross-sectional illustration taken along a longitudinal axis in a direction of I of FIG. 1D. FIG. 1F is a partial schematic cross-sectional illustration of the ocular implant of FIG. 1A, being in another representative operative state. FIG. 1G is a schematic cross-sectional illustration taken along a longitudinal axis in the direction of II of FIG. 1F.

According to some demonstrative embodiments, ocular implant 100 (FIG. 1A) may include a number of components, including, for example, a shunt 102, a fluid absorbing conduit 104, and a fluid drainage device 106. Shunt 102 includes a shunt fluid inlet 110, and a shunt fluid outlet 112, which define a shunt conduit 108 there between. Fluid absorbing conduit 104 may include a proximal end 114, an apical end 116 (defining a length of fluid absorbing conduit 104) and a port 120 (i.e., a fluid passageway aperture, hereinafter "fluid passageway aperture 120") of a variable area, denoted by A. Shunt conduit 108 couples between shunt fluid inlet 110 and shunt fluid outlet 112. Fluid absorbing conduit 104 may be mechanically coupled with shunt 102. Optionally, shunt 102 is mechanically coupled with fluid drainage device 106. FIG. 1A illustrates the general shape of ocular implant 100, where shunt 102 is substantially tubular, and fluid absorbing conduit is substantially in the form of a generally truncated hollow cone. As an optional feature, the truncated hollow cone may have a variable thickness. Proximal end 114 is coupled circumferentially with inlet 110.

The components of ocular implant 100 may optionally be constructed from various suitable polymers as described herein, and may also optionally be attached to each other through application of a solution of such a polymer or through application of a solution in which the polymer is miscible. The parts may alternatively optionally be joined using a connector (joint)—see FIG. 2D. Another way to fit the parts together is to optionally use an external elastomeric covering sheet (shell) which circumferentially covers (exteriorly) both fluid absorbing conduit 204 and shunt 202—see FIGS. 2B, 2C and 2E. The length of shunt 102 may optionally range between 2 and 3 mm; the area A of fluid passageway aperture 120 may optionally be in the range of 50-500 micrometer, fluid drainage device 106 may optionally have a diameter of 3-6 mm, and the length of fluid absorbing conduit 104 may optionally be in the range of 0.4-1 mm.

FIG. 1B illustrates the anatomy of a human eye 150, having a cornea 152, a part that is substantially transparent, which refracts and focuses incoming light (not shown) into eye 150 through a pupil 155 of an iris 156. A sclera 154 is a fibrous opaque white tissue covering eye 150, except for the portion covered by cornea 152. The border or the marginal region of cornea 152 by which it is continuous with sclera 154 is referred to as a limbus 158 (i.e., corneal limbus). A clear membrane, referred to as a conjunctiva 160, covers sclera 154. A lens 162 further focuses the incoming light refracted from cornea 152. An anterior chamber 164, anteriorly bounded by cornea 152, and posteriorly bounded by iris 156 and the middle part of lens 162, is a space filled with aqueous humour (i.e., aqueous). Aqueous, which is mainly produced by a ciliary body 166, flows to anterior chamber 164. Aqueous is removed (e.g., drained, filtered) from anterior chamber 164, in a normal eye, through a trabecular meshwork 168 into Schlemm's canal 170 (i.e., the scleral venous sinus), and thereafter, into the bloodstream (not shown). In a normal eye IOP is maintained and substantially determined by a balance between the production of aqueous and the removal thereof from anterior chamber 164. Elevated IOP (i.e., being higher than normal), such as, for example, in cases of ocular hypertension (OHT) is a significant risk factor contributing to the development of glaucoma. Elevated IOP in the case of OHT may optionally be characterized by an increased production of aqueous, or a decreased outflow of aqueous from anterior chamber 164.

According to some demonstrative embodiments, ocular implant 100 may optionally be operative according to various implementations, which depend on the location where ocular implant 100 is implanted (i.e., an anatomical implantation site), and the various surgical procedures employed for implantation. Examples of surgical procedures include trabeculectomy, deep sclerectomy, canaloplasty, and the like. The surgical procedures may be performed by use of an implant delivery device (not shown), such as a medical syringe, a needle, a probe, and the like. According to some embodiments, ocular implant 100 may be implanted in eye 150 via a trabeculectomy, at an anatomical implantation site illustrated in FIG. 1C. Accordingly, ocular implant 100 may be inserted into sclera 154 at limbus 158 (i.e., the limbal region) so that fluid absorbing conduit 104 protrudes into anterior chamber 164, as illustrated in FIG. 1C. In such a configuration, fluid absorbing conduit 104 may be substantially in fluid communication with aqueous of anterior chamber 164. Shunt fluid inlet 110 may be located substantially near anterior chamber 164, or substantially therein (i.e., in fluid communication therewith), whereas shunt fluid outlet 112 may be located exteriorly to anterior chamber 164. Hence, shunt fluid outlet 112 may be in communication with a space (not shown), external to anterior chamber 164. Fluid drainage device 106, which is in fluid communication with shunt fluid outlet 112, may be positioned substantially on the surface of sclera 154 underneath conjunctiva 160. Ocular implant 100 allows the conduction of intraocular fluid from anterior chamber 164 to pass (e.g., flow) through fluid passageway aperture 120, into fluid absorbing conduit 104, thereafter into shunt conduit 108, through shunt fluid inlet 110, and subsequently into fluid drainage device 106, through shunt fluid outlet 112. According to some embodiments, some of the aqueous fluid might back-flow (i.e., flow in the opposite direction to that mentioned above) due to capillary action, thus overcoming the tendency of the aqueous to escape anterior chamber 164 owing to sustained IOP. In such a case ocular implant 100 may further include one or more unidirectional valves (e.g., a check valve—not shown) to prevent back-flow into anterior chamber 164.

According to other embodiments, referring to FIG. 1B, the ocular implant (not shown in FIG. 1B) may optionally be implanted at the anatomical implantation site of Schlemm's canal 170. In this case, the shunt may be adapted (e.g., shape-wise) to fit at least partially in Schlemm's canal 170, for example, the shunt may be adapted to at least partially reside in canal 170, e.g., by having one or more portions of the shunt extending into Schlemm's canal 170. The portion of the shunt extending into Schlemm's canal 170 may optionally be formed into a shape that approximates the curvature of Schlemm's canal 170, in order to permit a substantial circumferential placement thereof there through. The dimensions of this portion of the shunt are therefore appropriate to the dimensions of Schlemm's canal 170. In some demonstrative embodiments, the shunt may be constructed from a flexible material that can be twisted and bent according to the tortuosity of Schlemm's canal 170. Further alternatively, the shunt may optionally be pre-formed, for example, into an arc shape, a T-shape, a V-shape, and the like.

According to some demonstrative embodiments, ocular implant 100 may optionally be implanted at the anatomical implantation site corresponding to a particular location along Tenon's capsule (i.e., the fascia bulbi—not shown). In this case, the ocular implant 100 may be inserted through the Tenon's capsule passing through sclera 154 and into anterior chamber 164. It is noted, that the ocular implant may optionally also pass through ciliary body 166 and trabecular meshwork 168 as well (FIG. 1B). In this case, fluid drainage device 106 may be placed beneath Tenon's capsule or alternatively, supra Tenon's capsule. Further alternatively, fluid drainage device 106 may be placed under a scleral flap (not shown). In this case a standard trabeculectomy flap (not shown) is made instead of removing corneal tissue during the medical procedure. Ocular implant 100 may then be inserted beneath the trabeculectomy flap into anterior chamber 164.

As noted previously, shunt conduit 108 couples between shunt fluid inlet 110 and shunt fluid outlet 112; furthermore, ocular implant 100 also features fluid absorbing conduit 104. As shown in FIG. 1C, the overall implant 100 may be placed within the eye such that implant 100 crosses the thickness of sclera 154, which may be 04-05 mm thick, in order for inlet 110 and fluid absorbing conduit 104 to enter into anterior chamber 164.

Reference is further made to two pairs of figures, each pair illustrating a particular representative operative state of fluid absorbing conduit 104: FIGS. 1D and 1E, and FIGS. 1F and 1G. Fluid absorbing conduit 104 may be composed from a material capable of expanding when absorbing the intraocular fluid and/or capable of contracting when desorbing from the intraocular fluid. When fluid absorbing conduit 104 expands, it is referred to as being in a fluid saturated state (shown in FIGS. 1F and 1G), and when fluid absorbing conduit 104 contracts, it is referred to as being in a fluid unsaturated state (shown in FIGS. 1D and 1E), respective to the amount of fluid (e.g., intraocular fluid) absorbed therein. Fluid absorbing conduit 104 is made from an absorbent material, a superabsorbent material, such as a hydrogel, a hydrocolloid, or combinations thereof (i.e., materials having the ability to absorb fluids). The extent of absorption depends on the nature of polymer from which the absorbing conduit 104 is formed. The absorption may also be dependent upon the amount of the aqueous humor existing in the anterior chamber of the eye. The higher the hydrophilicity of the polymer of absorbing conduit 104, the greater the amount of fluid that may be absorbed by the polymer.

According to some demonstrative embodiments, fluid absorbing conduit 104 may be made at least partially from a reversible absorbing material (i.e., capable of reverting substantially to its original state such as a dry state, a partial fluid saturated state). Examples of various materials constituting fluid absorbing conduit 104 will be detailed herein below.

FIG. 1D illustrates a partial schematic cross-sectional illustration of ocular implant 100 (i.e., of shunt 102 and fluid absorbing conduit 104), where fluid absorbing conduit 104 is in a fluid unsaturated state (i.e., substantially not engorged or swollen with intraocular fluid). In this state, fluid absorbing conduit 104 is contracted, as shown in FIG. 1D and an angle $\alpha_1$ (i.e., a particular fluid absorbing conduit angle) is formed between a longitudinal axis 190 and an inner surface 130 of fluid absorbing conduit 104. There is a direct correlation between the angle $\alpha_1$ and the fluid passageway aperture 120 diameter D1. The larger the fluid passageway aperture 120 diameter D1 the wider will be the angle $\alpha_1$.

FIG. 1E illustrates a partial schematic cross-sectional illustration of ocular implant 100 (i.e., of shunt 102 and fluid absorbing conduit 104) taken along longitudinal axis 190 in a direction of I of FIG. 1D, illustrating fluid passageway aperture 120 having a diameter $D_1$ and an area $A_1$. The length of fluid absorbing conduit 104 is denoted by $L_1$, its inner diameter varies from $D_1$ to $D_3$, and its outer diameter varies from $D_2$ to $D_4$. Shunt 102 has an inner diameter $D_3$ and an outer diameter $D_4$ (FIGS. 1D and 1E). When $\alpha_1$ is equal to 0 or 180 degree (when the diameter D1 of fluid passageway aperture 120 reaches its maximum) then D1=D3.

Although FIG. 1E illustrates that shunt 102 and fluid absorbing conduit 104 both have annular cross-sections (i.e., along longitudinal axis 190 in a direction of I), according to some demonstrative embodiments, the present invention is not restricted to a particular cross-section. For example, shunt 102 may possess a cylindrical cross-section, a rectangular cross-section, a hexagonal cross-section, a star-shaped cross-section, and the like.

FIG. 1F illustrates a schematic cross-sectional illustration of ocular implant 100, where fluid absorbing conduit 104 is in a fluid saturated state (i.e., substantially swollen with intraocular fluid). In this state, fluid absorbing conduit 104 is expanded, as shown in FIG. 1F and an angle $\alpha_2$ is formed between a longitudinal axis 190 and an inner surface 130 of fluid absorbing conduit 104. FIG. 1G illustrates a schematic cross-sectional illustration taken along longitudinal axis 190 in a direction of II of FIG. 1F, and illustrates fluid passageway aperture 120 having a diameter $D_5$ and an area $A_2$. The length of fluid absorbing conduit 104 in the fluid saturated state 104 is denoted by $L_2$, its inner diameter varies from $D_5$ to $D_3$, and its outer diameter varies from $D_6$ to $D_4$. Shunt 102 has an inner diameter $D_3$ and an outer diameter $D_4$ (FIGS. 1F and 1G). It is noted that $A_1 < A_2$ and $D_1 < D_5$.

As long as the hydrogel, i.e., the polymer from which fluid absorbing conduit 104 is formed, absorbs water, both the fluid passageway aperture 120 area A1 as well as the fluid passageway aperture 120 diameter D1 increase to result in A2 and D5, respectively, in which A2>A1 and D5>D1. As a result the rate of fluid drainage will be higher than the rate of fluid formation, thus a reduction in intraocular pressure may optionally be obtained.

In some demonstrative embodiments, fluid absorbing conduit 104, in the fluid saturated state (i.e., the expanded, fluid swollen state), may retain more intraocular fluid in comparison with that in the fluid unsaturated state (i.e., it is in a relatively higher fluid absorbency state). When fluid absorbing conduit 104 is in the fluid saturated state, fluid passageway aperture 120 has an area $A_2$, which is greater than the area $A_1$, therefore permitting more intraocular fluid to pass through fluid passageway aperture 120. Therefore, according to some embodiments, fluid passageway aperture 120 increases, when the absorption of intraocular fluid by fluid absorbing conduit 104 increases, and according to other embodiments fluid passageway aperture 120 decreases when desorption of intraocular fluid by fluid absorbing conduit increases. It is noted that although the pairs of FIGS. 1D and 1E and FIGS. 1F and 1G illustrate fluid absorbing conduit 104 in only two representative states, a virtually infinite number of states exist. In particular, fluid absorbing conduit 104 may optionally be in different states of absorbency, at a continuous range between that of fully saturated and fully unsaturated. Consequently, both the area, A of fluid passageway aperture 120, and the fluid absorbing conduit angle can assume a continuous range of values.

When the rate of production of intraocular fluid within anterior chamber 164 exceeds the rate of emission of the intraocular fluid, such as in individuals (e.g., patients with OHT or glaucoma, there is an increased accumulation of intraocular fluid within anterior chamber 164. As a result, the IOP within anterior chamber 164 increases and more intraocular fluid makes contact with fluid absorbing conduit 104. It is noted that increased IOP may optionally also occur from increased episcleral venous pressure (EVP). Fluid absorbing conduit 104 absorbs a portion (not shown) of the intraocular fluid, thus reciprocally decreasing the amount of intraocular fluid present within anterior chamber 164, which consequently, decreases the IOP within anterior chamber 164. Additionally, as fluid absorbing conduit 104 expands, the area A, of fluid passageway aperture 120 increases (FIG. 1F), thereby permitting more intraocular fluid to flow there through, and consequently, decreasing the IOP within anterior chamber 164 still further. Thus, excessive intraocular fluid is drained from anterior chamber 164 to fluid drainage device 106 (FIG. 1A), through fluid absorbing conduit 104 and shunt conduit 108.

Theoretically, the diameter D1 of fluid passageway aperture 120 can increase as a result of the absorption to a maximum which is equal to D3. The increase in both diameter D1 as well as area A1 of the fluid passageway aperture 120 occurs following the absorption of aqueous humor which exerts the needed for expanding the dimensions of the fluid passageway aperture 120 i.e. D1 and A1.

When the IOP within anterior chamber 164 decreases, such as, for example, when the rate of emission (e.g., via drainage, evaporation) of intraocular fluid from anterior chamber 164 exceeds the rate of production thereof, less intraocular fluid (i.e., that not already absorbed) makes contact with fluid absorbing conduit 104. Fluid absorbing conduit 104 desorbs (i.e., at least partially) from the intraocular fluid (e.g., via evaporation) and consequently, contracts (FIG. 1D). As a result of this contraction, the area A, of fluid passageway aperture 120 decreases (FIG. 1E), thereby limiting the outflow rate of intraocular fluid there through, and consequently, substantially maintaining IOP at a desired pressure range. IOP is maintained at such a level that prevents postoperative hypotony (i.e., substantially low IOP) from occurring.

In other words, regulation of IOP may be achieved in such a manner that when there is an increase of IOP, there is a respective increase in absorption of intraocular fluid by fluid absorbing conduit 104, which results in a respective increase of the area A, of fluid passageway aperture 120, permitting an increased outflow there through, consequently lowering the IOP. On the other hand, when there is a decrease of IOP, there is a respective decrease in absorption of intraocular fluid by fluid absorbing conduit 104, which results in a respective reduction of the area A, of fluid passageway aperture 120, thereby restricting outflow of intraocular fluid there through, consequently maintaining IOP at preferred pressure range.

Therefore, ocular implant 100 regulates IOP of intraocular fluid, contained within anterior chamber 164, to subsist in a desired pressure range, by controlling the rate of emission of intraocular fluid from anterior chamber 164. Ocular implant 100 may achieve a particular equilibrium (i.e., which is patient-dependent) between the rate of production of intraocular fluid within anterior chamber 164 and the rate of emission of intraocular fluid therefrom, respective of the EVP, in order to maintain IOP at a desired pressure range.

Fluid absorbing conduit 104 may optionally be made from a variety of materials, among which, preferably are, polymer materials. Various properties of the polymer materials may be taken into consideration in order to engineer a polymer or blend (i.e., a combination) of polymers that provide the desired utility and function. For example, according to Fick's laws of diffusion, the diffusion coefficient of the polymer may determine the rate of the diffusion of intraocular fluid into the polymer (i.e., into fluid absorbing conduit 104). The type of the polymer, its composition, thickness and the surface area of the polymer, exposed to intraocular fluid, are among several parameters which determine the rate and the degree of swelling of the polymer.

Fluid absorbing conduit 104 may be composed from a single polymer. Alternatively, fluid absorbing conduit 104 may be made of a blend of at least two different polymers. Different polymers may be employed, several of which, for example, listed according to a classification based on their method of preparation include homopolymers, copolymers (i.e., heteropolymers), block-copolymers, graft copolymers, and the like. Different types of block-copolymers may optionally be used, for example di-block copolymers, tri-block copolymers, multi-block copolymers, terpolymers, and the like. Furthermore, alternating copolymers, periodic polymers, random polymers, and statistical copolymers may optionally also make up fluid absorbing conduit 104. The polymer making up fluid absorbing conduit 104 may be a linear polymer, a cross-linked polymer, a thermoset (i.e., in case of a chemically cross-linked polymer), a thermoplastic polymer, combinations thereof, and the like. Essentially, the polymer constituting fluid absorbing conduit 104 is substantially hydrophilic as well as capable of swelling upon absorption of intraocular fluid. Preferably, the polymer is permeable to water-based fluids (e.g., intraocular fluid), water insoluble, generally non-biodegradable, and also biocompatible. When a water-permeable water insoluble hydrophilic polymer is employed, the polymer may optionally be that which has undergone cross-linking (i.e., a cross-linked polymer). A cross-link (not shown) is a connection (e.g., a chemical bond) that links one chain of the polymer to another chain. It is noted that cross-links may optionally be referred to as junctions. The degree of cross-linking (i.e., the cross-linking density) may determine the swelling capability of the polymer, and consequently, the rate of diffusion of intraocular fluid into fluid absorbing conduit 104.

Different kinds of cross-links exist (e.g., chemical cross-links, physical cross-links), having different properties and structures (e.g., multi-functional junctions, molecular entanglements). For example, chemical covalent cross-links are known to be thermally as well as mechanically stable, so once they are formed, they are difficult to break. Physical cross-links are reversible and may optionally be reformed by heat and dissolution. It is noted that the hydrophilicity of a polymer that has undergone cross-linking, for the purpose of becoming water insoluble, may optionally be preserved.

According to some demonstrative embodiments of the disclosed invention, a particular class of water absorbing polymer materials, that of hydrogels, has significant usefulness in the composition of fluid absorbing conduit 104. A hydrogel is a network of polymer chains, which are water insoluble and are typically cross-linked, in which water acts as the dispersion medium. Hydrogels are superabsorbent polymers (SAP), which can absorb and retain exceedingly large amounts of a liquid relative to their own mass. Generally, the term hydrogel, in view of the foregoing definition, is used to refer to a material that currently is in a swollen, fluid saturated state, however, when the network of polymer chains are in the desaturated, unswollen state, they become what is termed a xerogel (i.e., a dry gel). Hydrogels may optionally be cross-linked through chemical bonding (e.g., covalent bond cross-linking), forming chemical gels, or physical bonding techniques, thereby forming physical gels. Chemical gels may optionally be generally prepared by polymerization of monomers or by chemical cross-linking of water soluble polymers.

Unlike chemical gels, physical gels are formed by linking polymer chains through non-covalent bonds, such as hydrogen bonds, hydrophobic interactions, ion-mediation, entanglements, tetra-functional covalent cross-links, ligand-receptor type interactions, and the like. Physical gels differ from chemical gels in the type of cross-links, the apparent randomness of the polymer network formation, as well as the properties (e.g., network rigidity, elastic modulus) of the formed networks. Physical gels are reversible due to the physical cross-links having non-covalent type interaction among the polymer chains.

The degree to which a hydrogel swells may optionally be quantified according to, for example, the ratio of a sample volume in the swollen state to the volume in the dry state. Similarly, the degree of swelling may optionally be quantified according to weight (i.e., the ratio of the weight of a sample in the swollen state to that of the sample in the dry state). The degree of swelling $D_{SW}$, of a hydrogel is expressed in equation (1):

$$D_{SW} = \frac{W_{WET}}{W_{DRY}} \quad (1)$$

where $W_{WET}$ denotes the weight of the hydrogel in the wet, swollen, fluid saturated state, and $W_{DRY}$ denotes the weight of the hydrogel in the dry state (i.e., the xerogel, dry gel), where $D_{SW} \geq 1$. The swelling ratio $R_{SW}$, of the hydrogel is expressed in equation (2):

$$R_{SW} = D_{SW} \cdot \frac{d_0}{d_{SW}} \quad (2)$$

where $d_0$ denotes the density of the dry gel, and $d_{SW}$ denotes the density of the hydrogel in the swollen state. The extent of swelling of a hydrogel may optionally be dependent upon its hydrophilicity (i.e., or hydrophobicity), as well as the cross-linking density of its polymer chains, its ionic character, and its structure. For example, the presence of hydrophilic components in the polymer network can enhance the swelling characteristics of the polymer, whereas the presence of hydrophobic components generally diminishes the swelling competency of the polymer.

Fluid absorbing conduit 104 preserves its original shape throughout the swelling and unswelling processes, owing to the property of isotropic swelling of hydrogels. During swelling, the hydrogel expands, thereby increasing its size, while its original shape is substantially preserved. The response (e.g., expansion, contraction) of hydrogels to ambient environmental conditions may optionally be controlled. Ambient environmental conditions, to which hydrogels may optionally be responsive of, may include, for example, temperature, pH, ionic strength of the absorbed medium, relative humidity, ambient electromagnetic radiation to which the hydrogel is exposed, and the like.

Hydrogels of different types, each distinguishable according to their respective characteristic diffusion time, may be employed in the composition of fluid absorbing conduit 104. The diffusion time or diffusion time lag, defines the average time required for a particular type of molecule to permeate via diffusion a given distance through the medium (i.e., the hydrogel). Fluid absorbing conduit 104 may optionally be constructed to have a specific diffusion time, by the selection of particulars, such as the type of polymer, its composition, as well as the particular thickness of fluid absorbing conduit 104. Therefore, the time required for intraocular fluid to diffuse into fluid absorbing conduit 104 may optionally be controlled. On the other hand, the time required for fluid absorbing conduit 104 to desorb from intraocular fluid may optionally also be controlled. This is especially critical during the first post-operative period of two to three weeks following surgical implantation of ocular implant 100, when there is likelihood of hypotony of occurring. Parameters which influence the diffusion time include the thickness of the hydrogel, the hydrophilic nature of the hydrogel, as well as the cross-linking density of the polymer. Generally, the higher the cross-linking density of the polymer, the lower the rate of diffusion, and thus, the longer the resultant diffusion time. Likewise, the greater the thickness of fluid absorbing conduit 104, the longer the resultant diffusion time.

The chemical structure of the polymer may also affect the swelling ratio of hydrogels. For example, hydrogels containing hydrophilic groups (i.e., a polar group, one that can partake in hydrogen bond formation) swell to a higher degree compared to those containing hydrophobic groups (i.e., groups having essentially uniform electronic charge density). When hydrophobic groups are in the presence of water, they collapse so to reduce their exposure to the water. Consequently, hydrogels containing hydrophobic groups swell substantially less compared to hydrogels containing hydrophilic groups.

Hydrogels may optionally be classified according to sundry criteria. For example, classification of hydrogels may optionally be based according to their preparation method, according to ionic charges, according to structure, and the like. The class of hydrogels classified according to their preparation method include homopolymer hydrogels, copolymers hydrogels, multi-polymers, blockcopolymers, blend polymers (i.e., a mix of at least two polymers), and interpenetrating polymeric hydrogels. Homopolymers hydrogels contain (i.e., are derived from) a single type of hydrophilic monomer (i.e., -mer). A blockcopolymer is a polymer composed of at least two polymers (i.e., or oligomers) which are chemically linked together. Copolymer (i.e., heteropolymer) hydrogels are derived from two or more different types of constitutional units (i.e., monomers), where typically, at least one is hydrophilic. Multi-polymer hydrogels include three or more than three different types of monomers. It is noted that in some sense, copolymers hydrogels may optionally be considered multi-polymers. Interpenetrating polymeric hydrogels include at least two types of polymers, and involves swelling a network of the first type of polymer in the corresponding monomer of the second polymer, and constructing an intermeshing network the two types of polymers.

The class of hydrogels classified according to ionic charges includes anionic hydrogels, cationic hydrogels, neutral hydrogels, and ampholytic hydrogels. The class of hydrogels classified according to structure include amorphous hydrogels (i.e., where polymer chains are randomly arranged), semicrystalline hydrogels (having regions of ordered macromolecules), and hydrogen-bonded hydrogels. The following will detail the various substances and materials that fluid absorbing conduit 104 may optionally be made of, according to several of the different classifications of hydrogels. It is noted that fluid absorbing conduit 104 may function also as controllable drug delivery system (not shown), utilizing pharmaceutical agents (i.e., therapeutic agents—not shown).

Homopolymer Hydrogels

Homopolymers are polymers derived from a single type of monomer, which is the basic constitutional unit (i.e., repeating unit) of the polymer. Homopolymers can have cross-linked or uncross-linked structures, depending on the monomer itself, as well as the polymerization techniques employed (i.e., the methods used to chemically synthesize the polymer). Examples of cross-linked homopolymer hydrogels of the class of poly(hyroxyalkyl methacrylates) include poly(3-hydroxypropyl methacrylate (PHPMA), poly (glyceryl methacrylate) (PGMA), and poly(2-hydroxyethyl methacrylate) (PHEMA). PHEMA hydrogels are among the most widely studied and used of the synthetic polymer materials. Other polymers that expand upon hydration include HYPAN (Hydrolyzed polyacrylonitrile), cross-linked PVP poly(N-vinyl pyrrolidone), PVAm (polyacrylamide), PVA (polyvinyl alcohol), PEO (polyethylene oxide), and the like.

Copolymers, Block Copolymers, Polymer Blend Hydrogels, and Interpenetrating Polymer Networks (IPN)

Copolymer (i.e., heteropolymer) hydrogels are derived from two or more different types of constitutional units (i.e., monomers), which are arranged in a random, an alternating, or a block configuration, where typically, at least one monomer is hydrophilic. Examples of copolymer hydrogels that are combined with compatible monomers in order to impart the desirable properties to the hydrogels, include poly(N-vinyl pyrrolidone-co-2-hydroxyethyl methacrylate) poly (NVP-co-HEMA), poly(2-hydroxyethyl methacrylate-co-methyl methacrylate) poly(HEMA-co-MMA), poly(2-hydroxyethyl methacrylate-co-acrylic acid) poly(HEMA-co-AA), and the like.

Generally, different compositions may impart various properties to the hydrogel. For example, in order to reduce the rate of diffusion of intraocular fluid permeating into fluid absorbing conduit 104, it is possible to formulate a blend consisting of a hydrogel and a hydrophobic polymer. The hydrophobic polymer component in the resulting blend functions as a moderator of the rate of diffusion. Furthermore, such a blend may optionally be also formulated to attain other desirable properties, for example, to improve the mechanical properties of hydrogels (i.e., which typically suffer from low mechanical strength). It is noted that the constituents of the blend are either miscible or immiscible with each other. It is further noted that the addition of compatibilizers may be used to modify the blend.

The properties of the blends may optionally be varied by altering the ratio of each component in the blend. For example, the polymer may be a member of the family of polymers AQUAVENE. The hydrophilic family of polymers AQUAVENE includes a combination of a non-hydrophilic component (e.g., an elastomer such as urethane, silicone, PVC) and a hydrophilic component (e.g., a hydrogel), which allows the material to swell and further maintain strength. Furthermore, materials which have a tendency to depress the glass transition temperature of the hydrogel, thereby rendering the underlying polymer more ductile and less stiff, may optionally be added. Alternatively, materials such as fillers may optionally be added to reinforce the hydrogel polymer, thereby increasing its stiffness. Further alternatively, materials such as plasticizers may optionally be incorporated into the hydrogel polymer, in order to decrease its modulus of elasticity, which can lead to its softening.

Alternatively the hydrogel may be composed of block copolymers. Certain properties of block copolymers may optionally be varied by changing the ratio of hydrophilic to hydrophobic components. Examples of hydrogel based block-copolymers include hydrophilic polyether polyurethane, polyurethane diacrylate, Tecophilic TPU and Tecogel TPU, which are both thermoplastic polyurethane (TPU), and the like.

Tecophilic TPU and Tecogel TPU are hydrophilic segmented polyurethane from Thermedics-Noveon (Lubrizol). Both Tecophilic TPU and Tecogel TPU are from a family of aliphatic polyether-based TPU's, which have been specially formulated to absorb water. It is noted that Tecogel TPU is known to be melt processable using modified injection molding and extrusion methods.

According to an alternative composition of the polymer composing fluid absorbing conduit 104, the polymer may be an interpenetrating polymer network (IPN), based on a combination of a hydrogel and a hydrophobic (or hydrophilic) polymer. An interpenetrating polymer network is a polymer comprising two or more polymer constituents, forming a network, where at least one of which is synthesized or cross-linked in the presence of the other. The polymer constituents of the IPN are physically entangled, although they may be not covalently bonded to each other. Characteristically, IPNs have the capability to swell but not to dissolve in solvents, such as water. The following is a list of examples for the types of IPNs which may optionally be used to compose fluid absorbing conduit 104.

A semi-IPN is a polymer where one of the polymer constituents of the IPN is cross-linked and the other is a linear polymer. Another type of IPN is an AB cross-linked polymer, where two polymers are inter-cross-linked, thereby forming one network. Sequential IPNs may optionally be formed by polymerizing the first monomer, with a cross-linking agent, together with an initiator (i.e., or a catalyst) in order to form the network. Subsequently, the network is swollen with the second monomer and its respective cross-linking agent, and polymerized to form the IPN.

A simultaneous interpenetrating network (SIN) is an IPN formed by polymerizing two different monomers together with their respective cross-linking agents, in a single step.

Full IPNs are comprised of two networks that are juxtaposed, generating a substantial entanglements and interaction between the networks. A homo-IPN is a particular type of full-IPN, where both of the polymers used in the networks are the same (i.e., typically sequential IPNs). Thermoplastic IPNs possess at least one component which is typically a block copolymer. The other component is typically a semi-crystalline polymer or glassy polymer.

It is noted that IPN material composing fluid absorbing conduit 104 may optionally also be based on a combination of a hydrogel and a linear (i.e., a non-cross-linked) hydrophilic polymer, in which the hydrophilic polymer is either water soluble or water insoluble. In case the hydrophilic polymer is water soluble, fluid absorbing conduit 104 becomes porous after it comes in contact with intraocular fluid, thereby totally or partially dissolving the linear polymer.

The mechanical strength (e.g., the yield strength) of the hydrogel may optionally be enhanced by using a substantially hydrophobic polymer in the IPN. Alternatively, one or both of the macromolecular networks of the IPN could be biodegradable. A number of IPNs and semi-IPNs based on polysaccharides, such as chitosan and its derivatives, PNVP, PVA, poly(ethylene oxide) (PEO), poly(N-isopropyl acrylamide) (PNIPAM), PEG, and poly(methacrylic acid) (PMAA) may optionally be employed in hydrogel materials.

Non-Ionic Hydrogels

Non-ionic hydrogels (i.e., neutral hydrogels) are homopolymeric or copolymeric networks, which do not have charged groups in their polymeric structure. Generally, neutral hydrogels swell to equilibrium (i.e., swelling discontinues) when the effects of osmotic pressure of the solvent are counter-balanced with the chain stretching energy, required to resist the further swelling of the cross-linked polymer chains. The collapse and swelling of neutral hydrogel networks occur as a result of change in the ambient temperature.

Non limiting examples of non-ionic hydrogels include polyacrylamide (PAAm), poly(vinyl alcohol) (PVA), poly(ethylene glycol) (PEG), poly(ethylene oxide), copolymer of polypropylene oxide and polyethylene oxide (pluronic), poly(N-vinyl pyrrolidone), poly(methoxy-PEG methacrylate), N-isopropyl acrylamide and the like.

Ionic Hydrogels

Ionic hydrogels (i.e., polyelectrolytes) have charged groups in their polymeric structures. Ionic hydrogels include cationic hydrogels, anionic hydrogels, ampholytic and polyampholitic hydrogels. Anionic hydrogels may optionally be prepared, for example, by adding an excess of polyanions in polyelectrolyte complexes, by partial hydrolysis of poly(hydroxyl alkyl methacrylates), and the like. Anionic hydrogels exhibit a substantial increase in the swelling ratio, with a respective increase in the ambient pH. Examples of anionic hydrogels include polymers containing acidic groups incorporated within their molecular structure such as polymerizable acidic monomers, containing a carboxylic acid (e.g., acrylic acid, sulfonic acid), a sulfate or phosphate group (e.g., sulfo-ethyl acrylate, methacrylate, a sulfate or phosphate derivative of a hydroxyalkyl-acrylate or -methacrylate). Cationic hydrogel networks may optionally be synthesized, for example, by adding an excess of polycations through polyelectrolyte complexation reactions, by a partial hydrolysis of non-ionic preformed polymer networks, and the like. Examples of cationic hydrogels include polymers which incorporate a cationic monomer within their molecular structure. The cationic monomer is usually an ester of acrylic or methacrylic acid with an alcohol terminal amino group. The terminal amino group may be quaternized, such as dimethylaminoethyl methacrylate or acrylate, and the quaternized derivatives thereof. Such polymers may further be copolymerized with an additional acrylic monomer, such as alkyl acrylate or methacrylate, hydroxyalkyl acrylate or methacrylate, acrylamide, vinyl acetate, vinyl alcohol, and the like.

Polyampholytic hydrogel networks are macromolecules capable of possessing both positively and negatively charged moieties within the polymer network. Polyampholytic hydrogels are crosslinked networks composed of repeat units that are positively and negatively charged that exhibit different properties from polyelectrolyte polymers from which they originate. Examples of polyampholytic hydrogels include copolymers of acrylic acid and 2-vinylpyridine, copolymers of acrylic acid and 2-(Diethylamino)ethyl 2-methylacrylate, copolymers of 2-acrylamido-2-methyl-1-propanesulfonic acid (AMPS-H) and [3-(methacryloylamino)propyl]trimethylammonium chloride (MAPTA-C1), copolymers of acrylamide and an ionic complex of (N,N-diethylamino)ethyl methacrylate and acrylic acid, poly(N-isopropylacrylamide-co-sodium acrylate)/poly(ethyleneimine) [poly(NIPAM-co-SA)/PEI] and the like.

Polymeric hydrogel networks may optionally be further classified as hydrogen bonded, amorphous, or semi-crystalline, according to their structural characteristics, chemical bonding, and the like. Amorphous hydrogels (i.e., considered non-crystalline) are polymer networks containing randomly arranged macromolecular chains. Amorphous hydrogel networks can contain localized ordered structures, non-homogeneous structures, and the like. Semi-crystalline hydrogel networks are mixtures of amorphous and crystalline phases that contain regions of ordered macromolecular chains (i.e., crystallites). Typically, when semi-crystalline polymer networks are placed in aqueous medium, such as intraocular fluid, only the amorphous regions swell, while the crystalline regions are rendered unaffected by the aqueous medium.

Hydrogen-bonded hydrogels contain hydrogen bonds, between polymers, whereby physically cross-linked polymeric networks, such as IPNs, semi-IPNs, and thermoplastic polymers can result.

Chemical and Physical Biodegradable Hydrogels

Fluid absorbing conduit 104 may include biodegradable components. Generally, biodegradable substances decompose (i.e., break down) by the action of living organisms, such as bacteria, by enzymes, by acids, bases, salts, and the like. Biodegradable hydrogels may be classified into physical hydrogels and chemical hydrogels. Biodegradable chemical hydrogels may be further subclassified according to the site of degradation within the hydrogel networks. In case of biodegradable chemical hydrogels, the cross linker, for instance, may optionally be degradable and the part of hydrogel, which at first is completely insoluble, may later be degraded and dissolved.

The use of a particular type of biodegradable substance in the composition of fluid absorbing conduit 104 depends on the degradation mechanism of that substance. For example, the degradation process may optionally be utilized to control the degree of hydrophilicity, and ultimately, the rate of swelling of the polymer. An example of this may optionally be demonstrated in a blend of two or more polymers which compose fluid absorbing conduit 104, where one polymer is hydrophilic, and the other is biodegradable as well as hydrophobic. As the biodegradable hydrophobic polymer degrades with time (i.e., after implantation of ocular implant 100), the ratio of the hydrophilic component to the hydrophobic component increases correspondingly, thereby causing fluid absorbing conduit 104 to become more hydrophilic with time.

Polymers with a Degradable Polymer Backbone

Polymers with a degradable polymer backbone, which are employed in the composition of fluid absorbing conduit 104, are used to control particular properties thereof, such as the degree of hydrophilicity, the rate of swelling, and the like. Examples of biodegradable substances include polysaccharides and proteins, which constitute the polymer backbone of the hydrogels and are susceptible to enzymatic degradation. Their resultant degradation products have relatively low molecular weight and are generally water-soluble. On the other hand, polyesters, for example, are susceptible to hydrolytic degradation. Other examples include IPNs, semi-IPNs, and polymer blends in which properties such as the degree of hydrophilicity may optionally be controlled. Examples of such biodegradable blends include a blend of hydrophilic polymers and biodegradable polymers (e.g., polyvinyl alcohol (PVA), copolymer of poly(lactic acid) and poly(glycolic acid) (PLGA)), a blend of polyethylene oxide and poly(lactic acid)). Additional examples can include biodegradable block copolymers, having hydrophilic components such as PVA, polyethylene glycol (PEG), polyvinyl pyrrolidone (PVP), polyethylene oxide (PEO) or hydrophobic degradable components, such as polylactide, polyglycolide, poly butylene terephthalate (PBT), or other biodegradable polyesters, polyamides, polyurethanes, and the like.

Polymers with Degradable Cross-Linking Agents

Fluid absorbing conduit 104 may employ polymers having degradable cross-linkers (i.e., cross-linking agents), such as N,N-methylenebisacrylamide, oligomers, oligopeptides, and the like. The hydrogel network exhibits, at first, a substantially low degree of swelling due to the high density of cross-linking junctions between the hydrogel chains. A gradual increase in the degree of swelling follows due to an increase in the hydrophilicity and swelling of the hydrogel, owing to the gradual degradation of the cross-linkers within the hydrogel network.

Hydrogels with Degradable Pendant Groups

Hydrogels having degradable pendant groups (i.e., side groups) may optionally be employed to receive hydrogels having a deliberate hydrophilic scheme. For example, a polymer having pendant groups which possess hydrophobic properties, may exhibit greater hydrophilicity upon the removal of these hydrophobic pendant groups, thereby imparting the polymer increased swelling facility over time. It is noted that the degradation products of these hydrogels may not cause complete solubilization of the hydrogel. It is further noted that this approach may optionally be employed in cases where a graft copolymer of hydrophilic and hydrophobic polymers is employed. Such a graft copolymer may be insoluble and may have amphiphilic qualities. Examples of such polymers include polyacrylate or methacrylate containing alkyl ester pendant groups.

Entangled Polymer Networks

Fluid absorbing conduit 104 may optionally be constructed from various water soluble polymers. Different water soluble polymers tend to entangle with each other to form hydrogels, when their concentrations exceed a certain critical concentration value. When this happens, there is interpenetration between the polymer chains, causing the formation of an entangled network of polymers. Furthermore, when a shear force acts on this type of hydrogel, it may optionally behave as a solid as long as the shear stress is below a certain yield stress value, and as a viscous liquid otherwise. Examples of such hydrogels include those formed form biopolymers (e.g., hyaluronic acid, mucin, carboxymethyl cellulose). It is noted that hydration characteristics of such hydrogels may optionally be affected by parameters such as the pH of the dispersion medium, the ionic strength, and the like.

Ion-Mediated Polymer Networks

Fluid absorbing conduit 104 may optionally be at least partially made from in situ forming hydrogels. Examples include polysaccharides, which form gels upon the introduction of counterions in aqueous solutions. Other examples include alginates and pectins, which are able to form gels upon the introduction of divalent cations. Polysaccharides such as low-methoxy pectic, sodium alginate, and alginic acid, which are freely water soluble, may be converted to water insoluble polymers upon their exposure to a solution containing counterions such as $Ca^{2+}$ and $Mg^{2+}$. Thus, a composition containing water soluble polymers and calcium and magnesium salts such as calcium chloride and magnesium chloride, respectively, may produce a water insoluble hydrogel upon exposure to an aqueous medium. Chitosan forms gel in the presence of anions such as phosphates. The degree of cross-linking is dependent upon various factors such as the pH and ionic strength of the dispersion medium, the type of counterion, and the like.

Thermally-Induced Polymer Networks

Thermally-induced polymer networks may optionally be formed into hydrogels by lowering or raising their temperature. For example, thermally-induced hydrogels can thicken or gel when the temperature of the medium at which they are located changes. Examples of thermally-induced polymer networks include pectins having a high degree of methoxylation, hydrophobically derivatized chitosan, maltodextrin, poloxamer (PEO-PPO copolymer), poly(N-isopropylacrylamide) amylose, amylopectin, hydroxypropyl cellulose (HPC), and the like. Polymers such as gelatin and agar form gels by lowering the temperature of the solution containing them. Fluid absorbing conduit 104 may optionally be at least partially made of such thermally-induced polymer network, whereby that respective part, when implanted within eye 150 of the implantee, responsive to the body temperature of the implantee, forms into a hydrogel.

The following is a list of the various materials that may optionally be employed in the composition of fluid absorbing conduit 104. It is noted that the disclosed invention is not limited to only these materials. Examples of hydrogels include water insoluble polymers, such as poly(acrylic acid), poly(ethyl acrylic acid), poly(methacrylic acid), poly(α-propylacrylic acid), poly(sodium acrylate), poly(sodium methacrylate), poly(2-hydroxy ethyl methacrylate), polyacrylamide (PAM), poly(N,N-dimethyl acrylamide), poly (N-isopropyl acrylamide), poly(methacrylamide), poly(ethylene glycol) monomethyl ether, poly(ethylene glycol) monoethyl ether, poly(ethylene glycol) dimethyl ether, poly (ethylene glycol) monobenzyl ether, poly(ethylene glycol), poly(ethylene glycol) dibenzyl methylene terminated, poly (ethylene glycol) diethylamine and hydroxyl terminated, poly(ethylene glycol) diethylamine and methoxy terminated, poly(ethylene oxide), poly(ethylene oxide)-poly(propylene oxide) copolymers, poly(methyl vinyl ether), poly (styrenesulfonic acid) in undialysed form, poly (styrenesulfonic acid) in dialysed form, poly(styrenesulfonic acid cesium salt) in undialysed form, poly(styrenesulfonic acid cesium salt) in dialysed form, poly(styrenesulfonic acid sodium salt) in undialysed form, poly(styrenesulfonic acid sodium salt) in dialysed, poly(vinyl alcohol), poly(2-vinyl n-methyl pyridinium iodide), poly(4-vinyl n-methyl pyridinium iodide), poly(n-vinyl imidazole-quaternized with CH₃I), poly(2-hydroxyl ethyl acrylate-β-neopentyl acrylate), poly(hydroxyalkyl methacrylates) including poly(3-hydroxypropyl methacrylate) (PHPMA), poly(glyceryl methacrylate) (PGMA), poly(hydroxyl ethyl metacrylate), poly(2-hydroxyethyl methacrylate) (PHEMA), poly(2-hydroxyethyl methacrylate-β-neopentyl methacrylate), poly(2-hydroxy ethyl methacrylate-β-n-butyl methacrylate), poly(2-hydroxyl ethyl methacrylate-β-t-butyl methacrylate), poly(methyl methacrylate-β-2-hydroxyethyl methacrylate), poly(methyl methacrylate-β-2-hydroxyethyl methacrylate with cholesteryl chloroformate), poly(acrylic acid-β-methyl methacrylate), poly(methyl methacrylate-β-acrylic acid), poly(methyl methacrylate-β-sodium acrylate), poly(sodium acrylate-β-methyl methacrylate), poly(methacrylic acid-β-neopentyl methacrylate), poly(neopentyl methacrylate-β-methacrylic acid), poly(t-butyl methacrylate-β-ethylene oxide), poly(methyl methacrylate-β-sodium methacrylate), poly(methyl methacrylate-β-N,N-dimethyl acrylamide), poly(buta-1,2-diene-β-methylacrylic acid, poly(buta-1,4-diene-β-acrylic acid), poly(buta-1,4-diene-β-sodium acrylate), poly(buta-1,4-diene-β-ethylene oxide, poly(buta-1,2-diene-β-ethylene oxide), poly(buta-1,2-diene-β-ethylene oxide)-hydroxy benzoic ester terminal group, 4-methoxy benzyo-lester terminated poly(butadiene-β-ethylene oxide) diblock copolymer, poly(butadiene-β-N-methyl 4-vinyl pyridinium iodide), poly(isoprene-β-N-methyl 2-vinyl pyridinium iodide), poly(isoprene-β-ethylene oxide) (1,4 addition), poly(isoprene-β-ethylene oxide) (1,2 and 3,4 additions), poly(propylene-ethylene-β-ethylene oxide), and Pluronic polymers which are block copolymers based on ethylene oxide and propylene oxide. Further examples include hydrogenated poly(isoprene-β-ethylene oxide) (1,4-addition), hydrogenated poly(isoprene-β-ethylene oxide) (1,2-addition), poly(ethylene-b-ethylene oxide), poly(isoprene-β-ethylene oxide), poly(ethylene oxide-β-acrylic acid), poly(ethylene oxide-β-ε-caprolactone), poly(ethylene oxide-β-6-(4'-cyanobiphenyl-4-yloxy)hexyl methacrylate), poly(ethylene oxide-β-lactide), poly(ethylene oxide-β-Lactide), poly(ethylene oxide-β-2-hydroxyethyl methacrylate), poly(ethylene oxide-β-methyl methacrylate), poly(-methyl methacrylate-β-ethylene oxide), poly(ethylene oxide-β-methacrylic acid), poly(ethylene oxide-β-2-methyl oxazoline), poly(ethylene oxide-β-propylene oxide), poly(ethylene oxide-β-t-butyl acrylate), poly(ethylene oxide-β-tetrahydrofurfuryl methacrylate), poly(ethylene oxide-β-N,N-dimethylethylmethacrylate), poly(isobutylene-β-ethylene oxide), poly(styrene-β-acrylic acid), poly(styrene-β-sodium acrylate), poly(styrene-β-acrylamide), poly(p-chloromethyl styrene-β-acrylamide), poly(styrene-co-p-chloromethyl styrene-β-acrylamide), poly(styrene-co-β-chloromethyl styrene-β-acrylic acid), poly(styrene-β-cesium acrylate), poly(styrene-β-ethylene oxide), poly(4-styrenesulfonic acid-β-ethylene oxide), poly(styrene-β-methacrylic acid), poly(styrene-β-sodium methacrylate), poly(styrene-β-N-methyl 2-vinyl pyridinium iodide), poly(styrene-β-N-methyl-4-vinyl pyridinium iodide), poly(dimethylsiloxane-β-acrylic acid), poly(2-vinyl naphthalene-β-acrylic acid), poly(2-vinyl pyridine-β-ethylene oxide), poly(N-methyl 2-vinyl pyridinium iodide-β-ethylene oxide), poly(ethylene oxide-β-acrylic acid), poly(ethylene oxide-β-ε-caprolactone), poly(ethylene oxide-β-6-(4'-cyanobiphenyl-4-yloxy)hexyl methacrylate), poly(ethylene oxide-β-2-hydroxyethyl methacrylate), poly(ethylene oxide-β-methyl methacrylate), poly(-methyl methacrylate-β-ethylene oxide), poly(ethylene oxide-β-methacrylic acid), poly(ethylene oxide-β-2-methyl oxazoline), poly(ethylene oxide-β-propylene oxide), poly(ethylene oxide-β-t-butyl acrylate), poly(ethylene oxide-β-tetrahydrofurfuryl methacrylate), poly(ethylene oxide-β-N,N-dimethylethylmethacrylate), poly(isobutylene-β-ethylene oxide), poly(styrene-β-acrylic acid), poly(styrene-β-sodium acrylate), poly(styrene-β-acrylamide), poly(p-chloromethyl styrene-β-acrylamide), poly(styrene-co-β-chloromethyl styrene-β-acrylamide), poly(styrene-co-β-chloromethyl styrene-β-acrylic acid), poly(styrene-β-cesium acrylate), poly(styrene-β-ethylene oxide), poly(-styrenesulfonic acid-β-ethylene oxide), poly(styrene-β-methacrylic acid), poly(styrene-β-sodium methacrylate), poly(styrene-β-N-methyl 2-vinyl pyridinium iodide), poly(styrene-β-N-methyl-4-vinyl pyridinium iodide), poly(dimethylsiloxane-β-acrylic acid), poly(2-vinyl naphthalene-β-acrylic acid), poly(2-vinyl pyridine-β-ethylene oxide), poly(N-methyl 2-vinyl pyridinium iodide-β-ethylene oxide), poly(N-methyl 4-vinyl pyridinium iodide-β-methyl methacrylate), poly(N-methyl 4-vinyl pyridinium iodide-β-methyl methacrylate), poly(N-vinyl-2-pyrrolidinone) (PVP), poly(N-vinyl lactams), poly(N-vinyl caprolactam), polyvinylamines, hydrolyzed polyacrylonitrile (HYPAN) PEG-containing polyurethanes (polyurethane hydrogels) such as Aquavene, poly(ethylene oxide)/polyurethane composite hydrogel, Tecophilic TPU a hydrophilic, aliphatic, polyether-based thermoplastic segmented polyurethane and Tecogel TPU, from Thermedics-Noveon. Further examples yet include water insoluble or cross-linked polysaccharide gums such as low methoxy pectin, high methoxy pectin, sodium alginate, alginic acid, Arabic gum, guar gan, carrageenan, dextrin, dextran, starch, chitosan, chitin, galactomannan, cellulose, inulin, glycogen, gellan, agar, gum tragacanth, hyaluronic acid, glycosaminoglycan, locust bean, tamarind, karaya, furcellaran, heparin, curdlan sulfate, aloe vera polysaccharide, water insoluble or crosslinked cellulosic polymers such as; hydroxymethylcellulose, hydroxypropylcellulose, hydroxyethylcellulose, hydroxypropyl methylcellulose, methylcellulose, ethylcellulose, cellulose acetate, cellulose acetate phthalate, cellulose acetate trimellitate, hydroxypropyl methylcellulose phthalate, hydroxypropylcellulose phthalate, cellulose hexahydrophthalate, cellulose acetate hexahydrophthalate, carboxymethylcellulose, carboxymethylcellulose sodium, and microcrystalline cellulose, collagens, water insoluble crosslinked gelatin, cross-linked hydrolyzed gelatin, zein, shellac, combinations thereof, and the like.

Shunt 102 may optionally be made from a variety of materials. Preferably, shunt 102 is made from materials which can provide shunt 102 with a relatively high compressive strength, thereby imparting it with the capability to withstand the forces acting thereupon by the surrounding tissue (e.g., sclera 154). The materials composing shunt 102 may be biocompatible hydrophobic polymers, biocompatible metals, and the like. Examples of polymer materials used in composing shunt 102 include, polypropylene, polyethylene, polystyrene, polyfluoroethylene, polydifluoroethylene, polytetrafluoroethylene (PTFE), polyvinylchloride (PVC), polyvinylidene chloride (PVDC), polyalkylacrylate such as polymethylacrylate, polyethylacrylate, polybuthylacrylate, polyalkyl methacrylate such as polyethyl methacrylate, polybuthyl methacrylate, polymethyl methacrylate (PMMA), polyamides, stable polyesters, polyurethanes, polyureas, polysulfone, polysulfoxides, polyketones such as polyetheretherketon (PEEK), polyaldehydes, polycarbonate, polyimide, and the like.

Examples of biocompatible metal materials composing shunt 102 include stainless steel, platinum, gold, titanium, tantalum, nickel titanium alloys such as Nitinol, chrome cobalt alloys, and the like. Alternatively, substantially the same materials employed in the composition of fluid absorbing conduit 104 (mentioned herein above) may optionally be used in the composition of shunt 102. Furthermore, shunt 102 may be composed of biocompatible materials such as those employed for coating fluid absorbing conduit 104 such as elastomeric materials (mentioned herein below). In this case, shunt 102 is constructed with the required dimensions (e.g., wall thickness) that provide the necessary support for withstanding a possibility of its collapse under the forces exerted by the tissue surrounding shunt 102.

Alternatively, shunt 102 may be composed from materials different than those composing fluid absorbing conduit 104. Fluid drainage device 106 is made from a biocompatible material, and is substantially flexible. Fluid drainage device 106 is constructed to have a shape that conforms to the anatomical curvature of eye 150. Fluid drainage device 106 is operative to facilitate in the drainage of intraocular fluid from anterior chamber 164, to promote the formation of a normally functioning bleb (i.e., a sort of blister—not shown), and furthermore, to contribute in the mechanical coupling between ocular implant 100 and eye 150. Since bleb fibrosis (i.e., encapsulation and neovascularization of the bleb) can cause glaucoma implant failure, fluid drainage device 106 is constructed and operative to manage outflow of aqueous, and to ensure the development of a functional bleb. Bleb formation typically depends on tissue reaction to ocular implant 100 as well as pro-inflammatory substances in the aqueous. It is noted that fluid drainage device 106 may function also as controllable drug delivery system (not shown), utilizing pharmaceutical agents in order to aid, for example, in normal bleb formation. It is further noted that fluid drainage device 106 can have multiple drainage sites (not shown). It is noted that fluid drainage device 106 may optionally be made from various biomaterials such as acrylic, silicone, PTFE (polytetrafluoroethylene), ePTFE (expanded PTFE), polypropylene, materials composing fluid absorbing conduit 104 (mentioned herein above), elastomeric materials (mentioned herein below), and the like. Fluid absorbing conduit 104 may optionally be coupled to shunt 102 via an adhesive material (not shown), an elastomeric material, and the like.

Alternatively both shunt 102 and fluid absorbing conduit 104 can be completely or at least partially filled by a fluid absorbing material. According to some embodiments, the fluid absorbing material can be either the same or different than fluid absorbing conduit 104. In some demonstrative embodiments, the fluid absorbing material may have the ability to absorb, swell and/or consequently change the diameters D1 and/or D3.

Figure 2C:
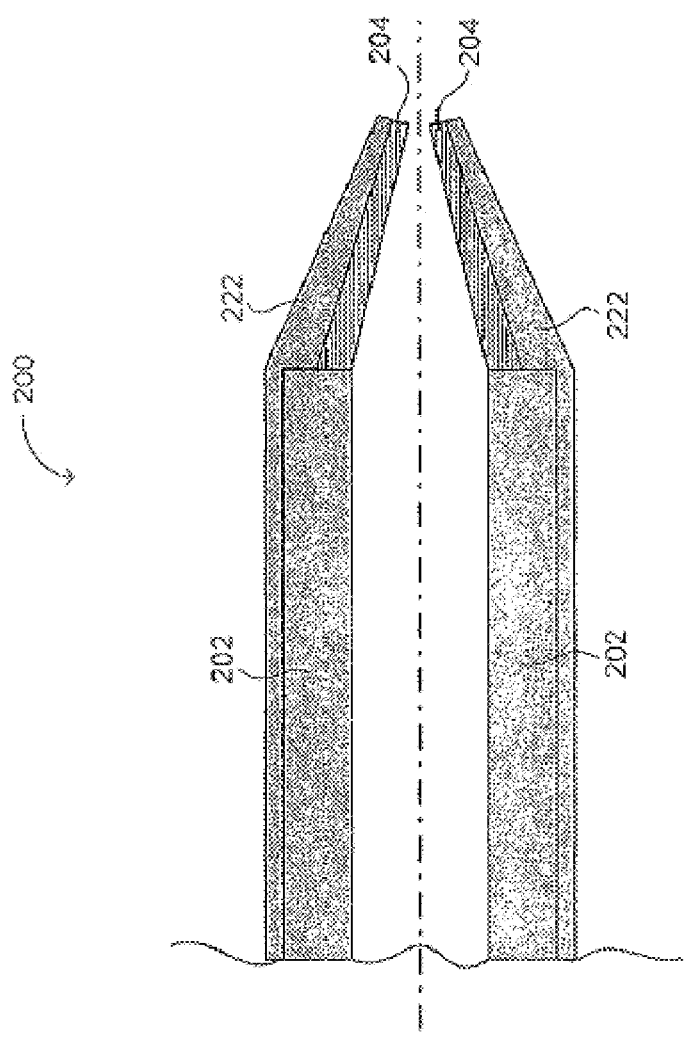
FIG. 2C is a partial schematic cross-sectional illustration showing a further configuration of the ocular implant of FIG. 2A.
Figure 2E:
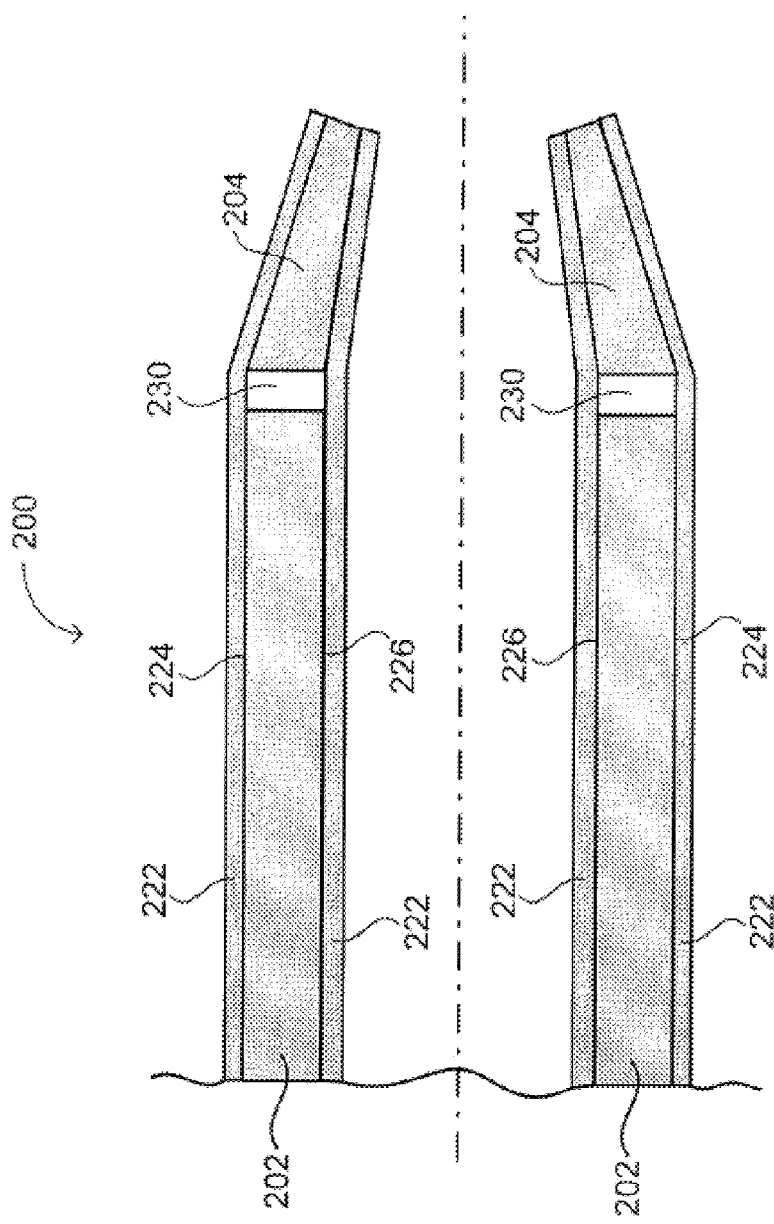
FIG. 2E is a partial schematic cross-sectional illustration showing a further configuration of the ocular implant of FIG. 2A.

Reference is now made to FIGS. 2A, 2B, 2C, 2D and 2E. FIG. 2A is a partial schematic cross-sectional illustration of an ocular implant, generally referenced 200, constructed and operative in accordance with another embodiment of the disclosed invention. FIG. 2B is a partial schematic cross-sectional illustration showing another configuration of the ocular implant of FIG. 2A. FIG. 2C is a partial schematic cross-sectional illustration showing a further configuration of the ocular implant of FIG. 2A. FIG. 2D is a partial schematic cross-sectional illustration showing another configuration of the ocular implant of FIG. 2A. FIG. 2E is a partial schematic cross-sectional illustration showing a further configuration of the ocular implant of FIG. 2A.

Ocular implant 200 is substantially similar to ocular implant 100 described herein above, except for the inclusion of an elastomeric material (e.g., an elastomer), which will be described herein below. FIG. 2A shows a partial schematic cross-sectional illustration of ocular implant 200, including shunt 202, fluid absorbing conduit 204 (i.e., substantially similar to fluid absorbing conduit 104 hereinabove), and elastomeric material 222. Shunt 202 is similar to shunt 102 as described herein above in connection with FIG. 1A. FIGS. 2B, 2C, 2D, and 2E illustrate various alternative configurations of ocular implant 200 of FIG. 2A.

Shunt 202 and fluid absorbing conduit 204 may be coupled with each other. Elastomeric material 222 may be coupled with fluid absorbing conduit 204, and may optionally also be further coupled with shunt 202. Elastomeric material 222 circumferentially covers an outer surface 218 of fluid absorbing conduit 204 along the length of fluid absorbing conduit 204. Alternatively, elastomeric material 222 may at least partially circumferentially cover outer surface 218 of fluid absorbing conduit, along at least a portion of the length of fluid absorbing conduit 204. Generally, elastomeric material 222 resists the expansion of fluid absorbing conduit 204 (i.e., during its expansion, swelling) and promotes the contraction of fluid absorbing conduit 204 (i.e., during its contraction). FIG. 2A illustrates that the width of fluid absorbing conduit 204 and that of elastomeric material 222 is less than the width of shunt 202. It is noted that fluid absorbing conduit 204 can have a greater width than that of shunt 202 (not shown). In an alternative configuration, shown in FIG. 2B, elastomeric material 222 may circumferentially cover (exteriorly) both shunt 202 and fluid absorbing conduit 204. In this configuration, fluid absorbing conduit possesses a width substantially equal to that of shunt 202. Further alternatively, elastomeric material 222 may at least partially circumferentially cover an outer surface 224 of shunt 202.

In another alternative configuration, shown in FIG. 2C, elastomeric material 222 may circumferentially cover (exteriorly) both fluid absorbing conduit 204 and shunt 202. In this configuration, the width of fluid absorbing conduit is substantially less than the width of shunt 202, and elastomeric material 222 may have a varying width. In a further alternative configuration, shown in FIG. 2D, elastomeric material 222 couples shunt 202 with fluid absorbing conduit 204.

Another alternative configuration is shown in FIG. 2E, where elastomeric material 222 couples fluid absorbing conduit 204 and shunt 202, such they are not mutually attached, but are separated by a space 230. As shown in FIG. 2E, elastomeric material 222 circumferentially covers (e.g., coats) fluid absorbing conduit 204 both exteriorly and interiorly. Elastomeric material 222 further circumferentially covers an outer surface 224 and an inner surface 226 of shunt 202. Space 230 provides flexibility (e.g., of movement) to ocular implant 200 during expansion and constriction of fluid absorbing conduit 204 at different states of intraocular fluid saturation. It is noted that the interior circumferential covering of both fluid absorbing conduit 204 and shunt 202 by elastomeric material 222, as illustrated in FIG. 2E, is optional. It is further noted, that in an alternative configuration, elastomeric material 222 partially circumferentially covers inner surface 226 and outer surface 224 of shunt and also partially circumferentially covers the inner and outer surfaces of fluid absorbing conduit 204 (not shown).

Elastomeric material 222 may be a hydrophobic elastic polymer material whose water absorption may be substantially low and preferably does not affect the inherent elastic properties of fluid absorbing conduit 204. Ocular implant 200 functions in a similar manner to ocular implant 100 as described in FIGS. 1A, 1B, 1C, 1D, 1E, 1F, and 1G, hereinabove, however, the further inclusion of elastomeric material 222 serves to enhance the capability of fluid absorbing conduit 204 to revert to a less fluid saturated state. When ocular implant 200 is implanted in the implantee, and fluid absorbing conduit 204 is in a substantially fluid saturated state (not shown), fluid absorbing conduit 204 swells and expands. Fluid absorbing conduit 204 is operative to at least partially overcome the elastic potential energy of elastomeric material 222. As fluid absorbing conduit 204 expands it elastically deforms elastomeric material 222 from its equilibrium state thereby substantially transferring this energy to elastomeric material 222 in form of elastic stored energy (ESE). Elastomeric material 222 in this higher elastic potential energy state, has a tendency to return to its equilibrium (i.e., lower elastic potential energy state), by applying external circumferential pressure about fluid absorbing conduit 204. Therefore, elastomeric material 222 can function to regulate the expansion and contraction of fluid absorbing conduit 204.

As fluid absorbing conduit 204 contracts (e.g., when at a low intraocular fluid absorbing state), elastomeric material 222 substantially reverts to its original shape and size owing to its inherent property of elastic recovery (ER). The circumferential exerted force applied by elastomeric material 222 to fluid absorbing conduit 204 is related to the amount of swelling and to the amount of intraocular fluid absorbed in fluid absorbing conduit 204. Accordingly, the higher the water uptake (i.e., absorption), the higher this circumferential force, and consequently, the higher the deformation of the elastomeric material 222 (i.e., higher elastic potential energy state). On the other hand, when fluid absorbing conduit 204 desorbs from intraocular fluid, this circumferential force decreases, and consequently, elastomeric material recoils (i.e., rebounds, is in a lower elastic potential energy state), leading to the ER thereof.

Elastomeric material 222 may optionally be composed from a variety of elastomeric polymers, which may optionally be thermosetic, materials requiring cross-linking or vulcanization, thermoplastics containing physical cross-linking, and the like. Generally, elastermeric material 222 possesses the properties of being elastic, relatively soft, flexible, deformable, an ability to be stretched to and to return substantially to its original size and shape (i.e., ER ability), and substantial absence of significant creep. Elastomeric material 222 may optionally be composed from homopolymers, copolymers, block-copolymers, block-co-polymers that exhibit a two-phase structure (e.g., rubbery at 37° C., and glassy at a temperature substantially above this). Examples of thermoplastic elastomers of block-copolymers include Kraton (from Shell chemicals), Pellethane (from Dow chemical), tecoflex (Thermedics-Noveon), Pebax, Arnitel (from DSM), Hytrel (from Du Pont), and the like.

Further examples of materials which can make up elastomeric material 222 include unsaturated rubbers that may optionally be cured by sulfur vulcanization such as Natural Rubber (NR), Synthetic Polyisoprene (IR), butyl rubber (copolymer of isobutylene and isoprene, IIR), halogenated butyl rubbers (Chloro Butyl Rubber: CIIR; Bromo Butyl Rubber: BIIR), polybutadiene (BR), styrene-butadiene rubber (copolymer of polystyrene and polybutadiene, SBR), nitril rubber (copolymer of polybutadiene and acrylonitrile, NBR), also called Buna N rubbers, halogenated nitril rubbers (HNBR) Therban and Zetpol, chloroprene rubber (CR) (polychloroprene, Neoprene, Baypren etc), saturated u) rubbers that cannot be cured by sulfur vulcanization such as EPM (ethylene propylene rubber, a copolymer of ethylene and propylene), EPDM rubber (ethylene propylene diene rubber, a terpolymer of ethylene, propylene and a diene-component), epichlorohydrin rubber (ECO), polyacrylic rubbers (ACM, ABR), silicon rubbers (SI, Q, VMQ), fluorosilicone Rubber (FVMQ), polydimethyl siloxane (PDMS) (silastic), fluoroelastomers (FKM, and FEPM, Viton, Tecnoflon, Fluorel, Aflas, and Dai-El), Perfluoroelastomers (FFKM, Tecnoflon PFR, Kalrez, Chemraz, Perlast), polyether block amides (PEBA), chlorosulfonated polyethylene (CSM), (Hypalon), ethylene-vinyl acetate (EVA), thermoplastic elastomers such as Elastron®, etc. thermoplastic vulcanizates (TPV), for example Santoprene® TPV, poly(styrene-isobutylene-styrene), thermoplastic polyurethane (TPU), thermoplastic olefins (TPO), the proteins resilin and elastin, polysulfide rubber, combinations thereof, and the like.

Alternatively, both shunt 202 and fluid absorbing conduit 204 can be completely or at least partially filled by a fluid absorbing material. In some demonstrative embodiments, the fluid absorbing material can be either the same or different than the fluid absorbing conduit 204. According to some embodiments, fluid absorbing material may have the ability to absorb, swell and/or consequently change the diameter D1 and/or D3.

Reference is now further made to FIGS. 3A, 3B, 3C, 3D, 3E, 3F, 3G, 3H, 3I, 3J, 3K, 3L, 3M and 3N, which show a plurality of partial schematic cross-sectional illustrations of various example shapes of the ocular implant, constructed and operative in accordance with a further embodiment of the disclosed invention. Ocular implants 100, and 200, described in the foregoing figures may assume a variety of shapes and configurations, in accordance with the disclosed invention, some examples of which are shown in FIGS. 3A to 3N.

In some demonstrative embodiments of the present invention, different parts constituting each shape and configuration of each figure can correspond with different respective parts of ocular implant 100. FIG. 3A illustrates a portion of the ocular implant being in the form of a generally arrow shape. This arrow shape having a tip portion 350 and a shaft portion 352. Tip portion includes a base 354 and an apex 356, and has a generally hollow frusto-conical shape. Base 354 includes a base opening 355, and apex 356 includes an apex opening 358. Apex 356 incorporates a sharp angled leading edge, as shown in FIG. 3A. Shaft portion 352 has a generally tubular shape. Shaft portion 352 is coupled substantially perpendicularly to base 354, coaxially with base opening 355. Alternatively, shaft portion 352 is coupled at various angles to base 354 (not shown). In one example, shaft portion 352 corresponds with (i.e., represents) shunt 108, whereas the tip portion 350 corresponds with (i.e., represents) fluid absorbing conduit 104. In another example, shaft portion 352 corresponds with elastomeric material 222. In a further example, tip portion 350 and shaft portion 352 may optionally be coated with elastomeric material 222 (not shown).

Figure 3B:
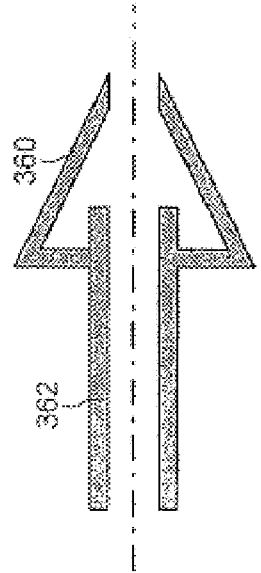
FIGS. 3A to 3N show a plurality of partial schematic cross-sectional illustrations of various example shapes of the ocular implant, constructed and operative in accordance with a further embodiment of the disclosed invention.
Figure 3D:
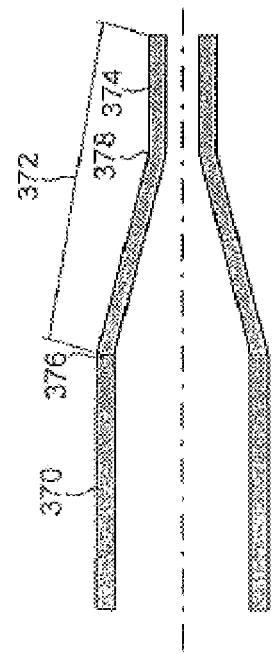
Figure 3A:
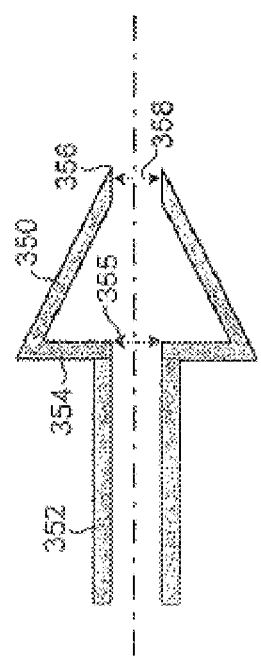

FIG. 3B illustrates the ocular implant being similar in shape to that illustrated in FIG. 3A, differing in that a shaft portion 362 (i.e., similar to shaft portion 352) partially extends into the hollow region of a tip portion 360 (i.e., similar to tip portion 350). Generally, this configuration may provide a relatively simple method of attachment between the shunt 108 and fluid absorbing conduit 104. Shaft portion 362 corresponds with (i.e., represents) shunt 108, and tip portion 360 corresponds with (i.e., represents) fluid absorbing conduit 104.

Figure 3C:
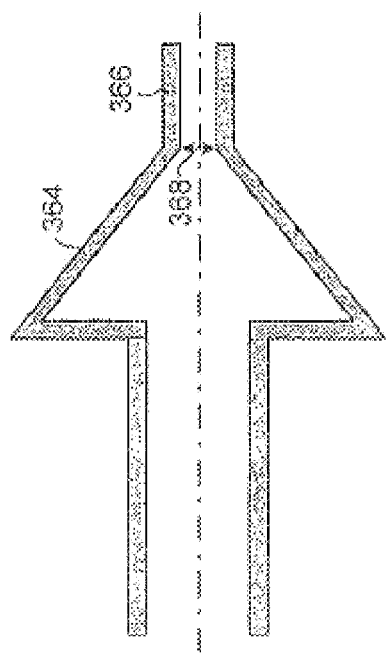

FIG. 3C illustrates the ocular implant being similar in shape to that illustrated in FIG. 3A, differing in that a tip portion 364 (i.e., similar to tip portion 350) further includes a front tubular extension 366, which is coupled circumferentially to tip portion 364 at an apex opening 368 (i.e., similar to apex opening 358) of tip portion 364.

FIG. 3D illustrates the ocular implant including a shunt 370 and a fluid absorbing conduit 372. Shunt 370 has a substantially tubular shape. Fluid absorbing conduit 372 includes a proximal end 376 and an apical end 378, and is substantially in the form of a generally truncated hollow cone incorporating a tubular section 374 that is circumferentially coupled to apical end 378. Fluid absorbing conduit 372 is coupled to shunt 370 at proximal end 376.

Figure 3E:
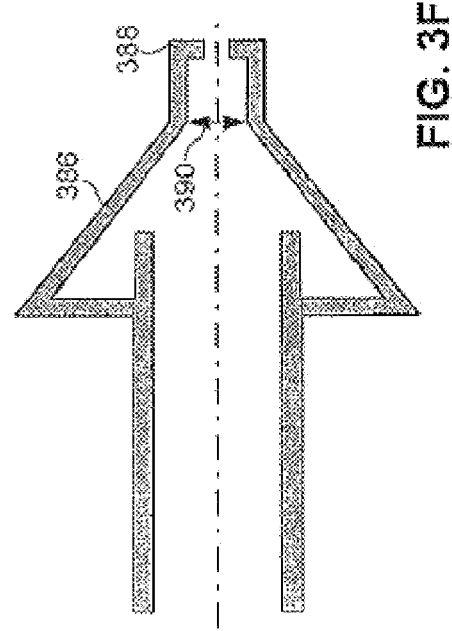

FIG. 3E illustrates the ocular implant including a shunt 380 and a fluid absorbing conduit 382. Shunt 380 includes two tubular sections, having different diameters, which are coupled coaxially together so that a portion of one of the tubular sections projects outwardly beyond the other (as shown in FIG. 3E). Fluid absorbing conduit 382 includes a proximal end 384 that incorporates tangential circumferential edge. Fluid absorbing conduit 382 is substantially in the form of a generally truncated hollow cone. Fluid absorbing conduit 382 is coupled circumferentially to shunt 380 at proximal end 384.

Figure 3F:
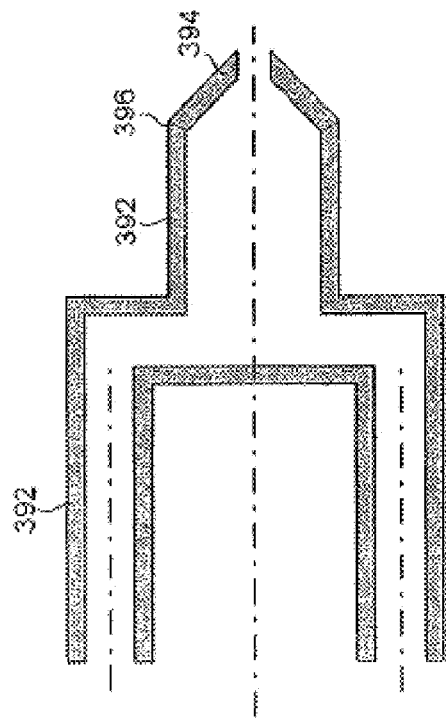

FIG. 3F illustrates the ocular implant being similar in shape to that illustrated in FIG. 3B, differing in that a tip portion 386 (i.e., similar to tip portion 360) further includes a front angled tubular extension 388. Tip portion includes an apex opening 390. Front angled tubular extension 388 is coupled circumferentially to tip portion 386 at apex opening 390.

Figure 3G:
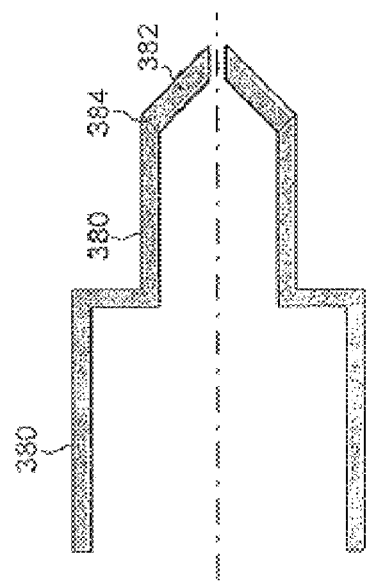
Figure 3H:
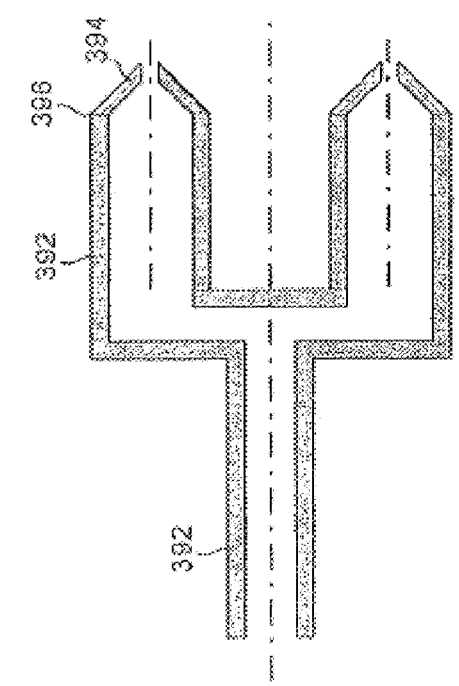

FIGS. 3G and 3H illustrate the ocular implant that includes a shunt 392 and at least one fluid absorbing conduit 394. Shunt 392 bifurcates into two substantially tubular sections (that are part of shunt 392) shown in both of FIGS. 3G and 3H. Each fluid absorbing conduit 394 includes a proximal end 396. Each fluid absorbing conduit 394 is substantially in the form of a generally truncated hollow cone. Each fluid absorbing conduit 394 circumferentially couples with at least one of the substantially tubular sections of shunt 392 at respective proximal end 396. It is noted that fluid the absorbing conduit and the shunt in all of these configurations may optionally be coated by an elastomeric material (i.e., similar to elastomeric material 222, illustrated in the aforementioned figures (not shown).

FIGS. 3I and 3J are partial cross-sectional illustrations of the ocular implant constructed according to another configuration, illustrating two different representative operative states. The ocular implant in this configuration includes a fluid absorbing conduit 304, an elastomeric material 322, and a shunt 302 having a shunt conduit 308. Fluid absorbing conduit 304 has a generally elongated shape, and extends at least partially along the length of shunt conduit 308. A portion of fluid absorbing conduit 304 protrudes exteriorly from shunt conduit 308, as shown in FIGS. 3I and 3J. Elastomeric material 322 partially circumferentially coats (i.e., covers) the portion of fluid absorbing conduit 304 that protrudes from shunt conduit (i.e., lengthwise). Elastomeric material 322 further exteriorly coats circumferentially (at least partially) shunt 302. In this manner, elastomeric material 322 couples between shunt 302 and fluid absorbing conduit 304. Fluid absorbing conduit 304, shunt 302, and elastomeric material 322 are similar respectively to fluid absorbing conduits 104 and 204, shunt 102 and elastomeric material 222.

FIG. 3I illustrates a partial cross-sectional view of the ocular implant at a particular operative state where fluid absorbing conduit 304 is unsaturated with fluid (i.e., intraocular fluid, aqueous). In this state, spaces 380 (i.e., within shunt conduit 308), unoccupied by fluid absorbing conduit 304, exist. When fluid absorbing conduit 304 comes in contact with the aqueous of the anterior chamber, it swells (i.e., saturates with intraocular fluid). As intraocular fluid diffuses through fluid absorbing conduit 304 (i.e., diffusing from the portion of fluid absorbing conduit 304 that protrudes to an outlet (not shown), representatively indicated by arrows 330), it causes fluid absorbing conduit 304 to expand, consequently taking up either wholly or partially (i.e., occupying, filling) spaces 380 as shown in FIG. 3J. FIG. 3J illustrates the operative state where fluid absorbing conduit 304 of the ocular implant is in a fluid saturated, swollen state.

FIGS. 3K and 3L are partial cross-sectional illustrations of the ocular implant constructed according to a further configuration, illustrating two different representative operative states. The ocular implant in this configuration includes a fluid absorbing conduit 306, an elastomeric material 324, and a shunt 310 having a shunt conduit 312. The configuration and operation of the ocular implant illustrated in FIGS. 3K and 3L are similar to those respectively shown in FIGS. 3I and 3J herein above, except that elastomeric material 324 is located within shunt conduit 312 extending at least partially along the length of shunt conduit 312, at least partially circumferentially coating fluid absorbing conduit 306. When fluid absorbing conduit 306 swells, intraocular fluid diffuses through fluid absorbing conduit 306 (i.e., representatively indicated by arrows 332), which causes fluid absorbing conduit 306 and elastomeric material 324 to expand into spaces 382 of shunt conduit 312, as shown in FIG. 3L. As fluid absorbing conduit 306 expands, it exerts force on elastomeric material 324, which also expands and causes it to deform (FIG. 3L in comparison with its original, fluid unsaturated state shown in FIG. 3K). When fluid absorbing conduit 306 is in a fluid unsaturated state it contracts, shown in FIG. 3K. Elastomeric material 324 enhances the capability of fluid absorbing conduit 306 to revert to a less fluid saturated state by the circumferential pressure which is applied thereto (i.e., in a similar manner described in relation with FIG. 2A, herein above).

FIGS. 3M and 3N partial cross-sectional illustrations of the ocular implant constructed according to another configuration, illustrating two different representative operative states. The ocular implant in this configuration includes a fluid absorbing conduit 314, and a shunt 316 having a shunt conduit 318. In this configuration, the longitudinal dimension of shunt 316, denoted by L, is considerably larger in comparison with the longitudinal dimension (i.e., that which is substantially parallel to shunt 316) of fluid absorbing conduit 314 (i.e., fluid absorbing conduit 314 is considerably shortened in comparison with fluid absorbing conduits 304 and 306 of FIGS. 3I and 3J, and 3K and 3L, respectively). Fluid absorbing conduit 314 is coupled with shunt 316 within shunt conduit 318. FIG. 3M illustrates fluid absorbing conduit 314 being in a fluid unsaturated state. FIG. 3N illustrates fluid absorbing conduit 314 in a fluid saturated state (i.e., swollen with intraocular fluid), whereby there is an increase of its dimensions (e.g., width) in comparison with the state shown in FIG. 3M. The opening of fluid absorbing conduit 314 in the fluid unsaturated state, illustrated in FIG. 3M, is denoted by $D_7$ and is smaller than the opening of fluid absorbing conduit 314 in the fluid saturated state, illustrated in FIG. 3N, denoted by $D_8$. The larger opening in the fluid saturated state, as shown in FIG. 3N, allows more intraocular fluid to drain from the interior chamber of the eye, in accordance with the disclosed invention. It is noted that in an alternative configuration, a plurality of discrete fluid absorbing conduits 314 are disposed along shunt conduit 318 (not shown).

Figure 4:
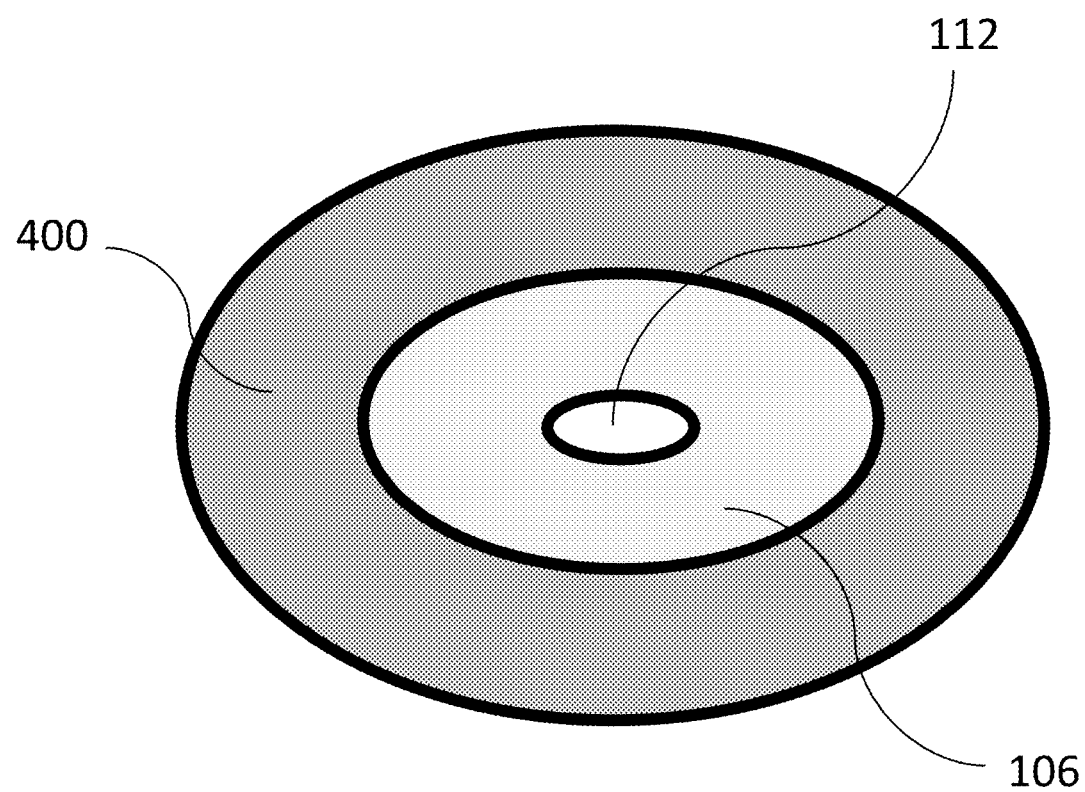
FIG. 4 shows an optional, illustrative embodiment of the implant with a biodegradable ring.

FIG. 4 shows an illustrative, non-limiting embodiment of the present invention wherein fluid drainage device 106 is further surrounded by a biodegradable ring 400 which may optionally be loaded with an active material such as an antiproliferative to hinder the progress of fibrosis process which may eventually block said shunt fluid outlet 112. The biodegradation process of biodegradable ring 400 alone or together with active material release may further assist hindering the progress of the fibrosis process. Biodegradable ring 400 comprises at least one biodegradable polymer to enable the total disappearing biodegradable ring 400 in the period of 2-3 weeks postoperative (post implantation).

The biodegradation duration may be controlled according to the composition of biodegradable ring 400. The factors such as the type of polymers from which biodegradable ring 400 is composed, the molecular weight of the polymers and water solubility of the polymers among others, are the main factors controlling the rate of the biodegradation process. Biodegradable ring 400 may also be composed of a mixture of polymers (blend) among which at least a polymer possessing biodegradation properties. The biodegradation process may optionally be based on one of the hydrolytic, enzymatic, dissolution, and dissolving processes and or a combination thereof. The inner diameter of biodegradable ring 400 is more or less the same as the outer diameter of said fluid drainage device 106 so that biodegradable ring 400 surrounds tightly said fluid drainage device 106. Biodegradable ring 400 is made of a biodegradable polymer which is more preferably a flexible polymer in order to match the arch shape of the posterior portion of the eye. Biodegradable ring 400 may optionally also be made of a polymer which is not initially flexible but may optionally become flexible following the absorption of liquid from the surface of the eye. Biodegradable ring 400 is preferably designed to minimize potential for ocular motility disturbances. Example of active materials which may optionally be loaded in biodegradable ring 400 may optionally include but are not limited to immunosuppressive drugs such as azathioprine which is a prodrug converted to 6-mercaptopurine and metabolised to cytotoxic thioguanine nucleotides which are responsible for immunosuppression and inhibiting DNA synthesis; alcineurin inhibitors which catalyse some of the intracellular processes associated with the activation of T-lymphocytes; cyclosporin which is an immunosuppressant used in transplantation, tacrolimus which is a macrolide antibiotic but is also a calcineurin inhibitor, antiproliferative drugs such as sirolimus (rapamycin) and everolimus which are structurally very similar and have the same mechanism of action, mycophenolate which is the prodrug of mycophenolic acid and which inhibits purine synthesis by inhibiting inosine monophosphate dehydrogenase, antithymocyte globulin, antibodies against CD2x such as basiliximab and daclizumab which are monoclonal antibodies against CD25, muromonab-CD3 which is a mouse-derived monoclonal antibody which binds to the CD3 component of the T-cell receptor complex and which is also associated with the cytokine release syndrome, sodium butyrate which a proliferation inhibitor and any combination thereof.

The terms "degradation", "biodegradation" and "bioerosion" are used herein interchangeably and refer to the conversion, the decomposition, or the breakdown of substances by either enzymes or acid or base or any other aqueous media such as a buffer or saline. The biodegradation process can therefore be based on one of the hydrolytic, enzymatic, dissolution, and dissolving processes and or a combination thereof. Typically, substances undergoing biodegradation are broken down into intermediate or end products (i.e., degraded products) by processes such as solubilization, simple hydrolysis, the action of biologically formed entities, the action of biological agents (e.g., enzymes, microbes), and the like. It is noted that polymer molecules undergoing biodegradation may not necessarily break down into smaller or simpler intermediate products.

In particular, bioerosion substantially involves both physical processes (e.g., dissolution), as well as chemical processes (e.g., hydrolysis). Alternatively, bioerosion can involve, for example, a water insoluble polymer that turns into a water soluble polymer under certain physiological conditions (e.g., ion-crosslinked polymers such as polysaccharides).

Biodegradable ring 400 may optionally be made from different types of biodegradable polymers, such as those made from thermoplastic or thermosetting materials. Alternatively, biodegradable ring may optionally be made from cross-linked or linear polymers, which are crystalline or amorphous polymers. Alternatively further, biodegradable ring may optionally be made from polymers, which are plasticized or those which are non plasticized. Alternatively further, biodegradable ring may optionally be made from polymers that are blended or mixed with other biodegradable polymers. Biodegradable ring may optionally be made from polymers which are copolymers, homopolymers, blockcopolymers, graftcopolymers, segmented blockcopolymers, shape memory polymers (SMPs) which may optionally be made from hybrid or composite materials, and the like. Biodegradable ring may optionally be made from polymers, exhibiting surface erosion, those exhibiting bulk erosion, or their combination, for realizing the preferred release profile of active material and also for controlling the degradation mechanism and the rate of biodegradation of biodegradable ring in accordance with fibrosis process. Surface erosion polymers have water labile linkages, and are typically hydrophobic entities. Hydrolysis of such polymers is initiated on the outer surface and maintained thereon. Examples of surface erosion polymers include polyanhydrides such as, poly(carboxyphenoxy hexane-sebacic acid), poly(fumaric acid-sebacic acid), poly(carboxyphenoxy hexane-sebacic acid), poly(imide-sebacic acid)(1:1), poly(imide-carboxyphenoxy hexane-)(2:3), and polyorthoesters (i.e., diketene acetal based polymers).

Bulk erosion polymers have water labile linkages and are typically hydrophilic entities. Hydrolysis of such polymers occurs within, as well as on the outer surface, of the polymer, hence they exhibit bulk erosion. Examples of bulk erosion polymers include poly(-hydroxy esters) such as poly(glycolic acid), poly(lactic acid), poly(caprolactone), poly(p-dioxanone), poly(trimethylene carbonate), poly(oxaesters), poly(oxaamides), and their co-polymers and blends. Examples of commercial bulk erosion polymers include poly(dioxanone), poly(glycolide), poly(lactide)-PLLA, poly(lactide/glycolide), poly(glycolide/caprolactone (75/25) and poly(glycolide/trimethylene carbonate). Other examples of bulk erosion polymers include but are not limited to tyrosine derived polyamino acids (e.g., poly(DHT carbonates), poly(arylates), poly(imino carbonates), phosphorous containing polymers (e.g., poly(phospoesters), poly (phosphazenes)), poly(ethylene glycol) (PEG) based block co polymers (e.g., PEG-PLA block-copolymer, PEG-poly (propylene glycol) block-copolymer, PEG-poly(butylene terphthalate) block-copolymer and etc.), poly(-malic acid), poly(ester amide), and polyalkanoates (e.g., poly(hydroxybutyrate) (HB), poly(hydroxyvalerate) (HV) co-polymers).

Alternatively, biodegradable block-copolymer may optionally be made from combinations of surface and bulk erosion polymers in order attain the desired drug delivery, physical and chemical properties and further to control the degradation mechanism. For example, a plurality of polymers may be blended together in order to attain a polymer with a specific degradation rate. The combination or blend (i.e., either miscible or immiscible) of different polymers may optionally also be used for attaining the required properties of biodegradable ring. The required properties of the combination typically include ductility, durability, flexibility, toughness, tackiness, adhesion and cohesion. It is noted that additional materials such as compatibilizers may be used to modify the blend. The blend may optionally be supplemented with additional materials, which modify the glass transition temperature (i.e., the temperature at which the polymer becomes soft at heating or brittle on cooling) of biodegradable ring thereby rendering the polymer more ductile and less stiff. For example, blending different types of polymers may produce a blended material having high ductility and high stiffness. Polymers having high stiffness such as poly(lactic acid), poly(glycolide) and poly(lactide-co-glycolide) copolymers blended with ductile polymers such as poly(caprolactone), poly(dioxanone) and polyurethane, can result in a material having high toughness, high stiffness, and high ductility. The polymer may optionally be synthesized from soft polymers and stiff polymers, combined in different ratios. It is further noted that elastomeric copolymers, terpolymers, and macromers may optionally be employed in order to achieve the desired properties for biodegradable ring. Further alternatively, biodegradable ring may optionally be constructed in layers, whereby a surface erosion polymer (not shown) coats a bulk erosion polymer (not shown). It is noted that biodegradable ring is preferably made from a material that is biocompatible.

The major classes of biodegradable polymers that may optionally be employed are, without limitation, polyesters, polyanhydrides, tyrosine derived polycarbonates, polyorthoesters, polyurethanes, polydioxanone or poly p dioxanone, polyphosphazenes and water soluble polymers. The following will detail the various substances and materials that biodegradable ring may optionally be made of, according to the different classes (i.e., families) of biodegradable polymers.

Non-limiting examples of polyesters include polyhydroxy acids such as poly(L-lactide), poly(D-lactide), poly(D,L-lactide), poly(glycolide), poly(L-lactide-co-D,L-lactide), poly(L-lactide-co-glycolide), poly(D,L-co-glycolide), poly(1,3-propylenemalonate-co-glycolide), polymalic acid, poly(epsilon-caprolactone), poly(1,3-propylenemalonate-co-lactide), poly(1,3-propylenemalonate-co-dio-xanone), polyhydroxybutyrate, polyhydroxyvalerate, polycarbonates, poly(glycolide-co-trimethylene carbonate), poly(glycolide-co-beta-propi-olactone), poly(glycolide-co-gamma-butyrolactone), poly(glycolide-co-delta-valerolactone), poly(glycolide-co-epsilon.-cap-rolactone), poly(lactide-cotrimethylenecarbonate), poly(lactide-co-delta-propiolactone), poly(lactide-co-delta-butyrolactone), poly(lactide-co-delta-valerolactone), poly(lactide-co-delta-caprolact-one) having the chemical structural formula of [O—(CH2)x-O—CO—(CH2)y-OC-]n, where x=1-8 and y=1-8, polyethylene adipate (PEA), polyethylene carboxylates: polyethylene succinate, polyethyleneoxalate, polyethlene subarate, polyethlene azelate, polyethylene sebacate, polytetramethylene carboxylates: polyteteramethylene succinate, polyhexamethylene carboxylates, and polydiethylene oxide carboxylates.

Non-limiting examples of commercial biodegradable polyesters include polyhydroxyalkanoates (PHA), polyhydroxybutyrate (PHB), polyhydroxyhexanoate (PHH), polyhydroxyvalerate (PHV), polylactic acid (PLA), polyglycolic acid (PGA), poly(glycolic-co-lactic acid), polydioxanone (PDO), polyvalerolactone (PVL), polycaprolactone (PCL), polytarteronic acid, polymalonic acid, polybutylene succinate (PBS), polybutylene succinate adipate (PBSA), polyethylene adipate (PEA), polyethylene succinate (PES), aliphatic-aromatic copolyesters (AAC), polyethylene terephthalate (PET), polybutylene adipate/terephthalate (PBAT), and polymethylene adipate/terephthalate (PTMAT) and may optionally also be employed. Other polymers that may optionally be employed are polyactones (e.g., poly(caprolactone) (PCL), poly(propylene fumarates) (PPF), poly-hydroxybutyrate-co-polyhydroxyhexanoates (PHBH) which are naturally produced polyesters, polybutylene succinate (PBS) which is a synthetic aliphatic polyester, aliphatic-aromatic (AAC) copolyesters, and modified polyethylene tetraphalate (PET), polyanhydrides including poly[1,6-bis(carboxyphenoxy)hexane]), poly(anhydrides-co-imides) such as poly-[trimellitylimidoglycine-co-bis(carboxyphenoxy)hexane], and poly[pyromellitylimidoalanine-co-1,6-bis(carbophenoxy)-hexane], tyrosine-derived polycarbonates including polycarbonates derived from ethyl, butyl, hexyl, and octyl esters of desaminotyrosyl-tyrosine (e.g., poly(desaminotyrosyl-tyrosine-ethyl) ester carbonate (PDTE carbonate)), polyorthoesters including polymers based on an alkyl orthoformate or orthoacetate such as methyl orthoformate, ethyl orthoformate, methyl orthoacetate, and ethyl orthoacetate, combinations thereof, and the like, polyurethanes including segmented polyetherurethane or polyetherurethane uerea, where the polyether may be polytetramethylene glycol, polypeopylene glycol, polyethylene glycol, and combinations thereof. Further non-limiting examples of PU include polyesterurethane or polyesterurethane urea, where the polyester may be polyethylene succinate, polyethylene adipate, polybuthylene succinate, polybuthylene adipate, combination thereof, and the like, polydioxanone (or poly-p-dioxanone), polyphosphazenes such as poly[(50% ethylglycinato) (50% pmethylphenoxy) phosphazene] and combinations thereof.

As it has previously been mentioned the process of biodegradation (not shown) of biodegradable ring 400 can involve various mechanisms of biodegradation, some of which may optionally be classified according to mechanisms of solubilization, chemical hydrolysis, enzymatic degradation, and other mechanisms, such as those employing ion-exchange. Biodegradable ring 400 may optionally be made from materials that biodegrade according to each of these mechanisms or to combinations thereof.

Generally, solubilization refers to the ability of a substance, such as water-soluble polymers, to dissolve in a solvent such as water. Various water-soluble polymers may optionally be considered biodegradable because of their ability to absorb water and to dissolve. The composition of biodegradable ring, without limitation, may optionally include at least one hydrophilic polymer. Without limitation, water-soluble hydrophilic polymers may consist of, for example, polyhydroxyethylmethacrylate (PHEMA), polyacrylic acid, polyacrylamid, polymethacrylates and their copolymers, polyvinyl alcohol (PVA), polyethylene oxide, dextrans, polyvinylpyrrolidone (PVP) copolymer of PVP and polyvinyl acetate, cellulose derivates such as hydroxypropyl cellulose, carboxy methyl cellulose, hydroxymethyl cellulose hydroxyethyl cellulose, hydroxypropyl methylcellulose modified cellulose, polysaccharides, collagen, gelatin, hydrolyzed gelatin, polypeptides, polysaccharide, modified polysaccharide, gums and the like.

Non-limiting examples of gums include heteropolysaccharides (e.g., xanthan gums), homopolysaccharides (e.g., locust bean gum), polysaccharide gums such as hydrocolloids, and any combination thereof. Further non-limiting examples include galactans, chitosan, welan gum, indian bedellium, pectin, agar, vegetable gums (e.g., alginates), acacia, tara gum, tragacanth, mannans, karaya gum, hibiscus, Accaroid/Yacca/Red gum, agar, deacetylated xanthan gum, myrrh gum, karaya, ester gum, sodium alginate, ipil-ipil seed gum, tamarind gum, alginic acid, carrageenan, acacia *catechu*, letuca, polycarbophil, panicum, detarium gum, dammar gum, treculia *africana* gum, carbobrotus, ghatti gum, salai guggal, copaiba gum, Colocassia *esculenta* gum, asafetida, cambi gum, malus, enterolobium cyclocarpum, mastic gum, sodium polypectate, gluten, benzoin gum, xanthan gum, glycine, *cassia* gum, sandarac, gambier gum, butea *frondosa*, cucumis, konjac mannan, Prosopis Africana gum, poliathus, gum Talha, pectin, aptenia, guar gum, khaya gum, zea, actinidia, chickorium, scleroglucan, carob gum, oryza, mesembryanthemum, medicago, sida, solanum, gellan gum, Hakea gibbosa gum, locust bean gum, juniper gum, afzelia *africana* seed gum, glucomannan, hordeum, trifolium, trigonella, galactan gum, lycopersicon, phleum, tragacanth, phalaris, and any combination thereof.

Without wishing to be limited by a single hypothesis, the degradation process of hydrophilic polymers involves the diffusion of the water into the hydrophilic polymers, and leads to the formation of a swollen system (not shown), which ultimately dissolves upon a further uptake of water. The degree of swelling and dissolution of the hydrophilic polymer may depend on the specific hydrophilicity of the polymer, the interaction between polymers, the interaction between the polymer and water, and the molecular weight of the polymer. It is noted that environmental variations in temperature, pH, and ionic strength may also influence the process of solubilization. Alternatively the degradation process of hydrophilic polymers may mainly involve erosion at the surface and swelling process may optionally be a secondary process.

Chemical hydrolysis is a type of reaction used to break down polymers. In general, chemical hydrolysis is a process or a chemical reaction in which a chemical compound reacts with water. There are myriad polymers which can undergo chemical hydrolysis and which may optionally be employed in biodegradable ring 400. Non-limiting examples of such polymers include polyhydroxybutyrates, polyurethanes, polyphosphates, polylactic acid, polyglycolic acid, copolymers of glycolic and lactic acid, polyorthoesters, polylactones, polydioxanones, polyesters, polylactones, polyhydroxyvalerates, and polyanhydrides. These polymers have linkages that are susceptible to water, and can undergo chemical hydrolysis, which eventually may cause the breakage of these linkages.

Enzymatic hydrolysis is a process where enzymes (i.e., biomolecular catalysts) are used to break down molecules, such as starch, or cellulose, into smaller molecules, such as sugar. Examples of such enzymes include hydrolases, which are a group of enzymes that catalyze the hydrolysis of chemical bonds (e.g., C—O bonds, C—N bonds, C—C bonds). Therefore, hydrolases are useful in the degradation of various proteins, polyurethanes, polyureas, polysaccharides, and the like. Other examples of compounds that degrade by enzyme catalysis are polypeptide or poly α-amino acids. Enzymes known as glycosidases can hydrolyze polysaccharides, starch, and dextran, used in the preparation of biodegradable hydrogels. It is noted that many synthetic polymers, such as polydiols and polyvinyl alcohol are also known to undergo degradation by enzyme catalysis. Various parameters may optionally be modified in order to obtain a biodegradable material, used for biodegradable ring, with the desired degradation properties.

Ion-exchange involves the exchange of ions between two electrolytes (i.e., or between an electrolyte solution and a complex). Ion-exchange can lead to the solubilization of the polymer being in contact with a particular medium (e.g., water). The solubility and dissolution of polymers may be pH dependent. Therefore, the selection of biodegradable ring having particular degradation properties may optionally be partially based on considerations such as pH dependency on solubilization of the polymeric material from which biodegradable ring is made. Polyacids and polybases may optionally be used for formulating such a polymeric material. Furthermore, polymers which are soluble only in acidic pH, basic pH, or neutral pH, may optionally be used. Non-limiting examples of polymers that may optionally be employed include hydroxypropylmethylcellulose phthalate, cellulose acetate phthalate, polyvinylacetate phthalate, hydroxypropylmethylcellulose acetate succinate, poly (methacrylic acid, methyl methacrylate)(1:1) and poly (methacrylic acid, ethyl acrylate)(1:1), alginic acid, and sodium alginate. It is noted that there are several water-insoluble polymers that form soluble macromolecules by the process of ion-exchange. Non-limiting examples of such water-insoluble polymers include divalent metal salts of polyanions (e.g., calcium salt of alginic and pectic acids).

Biodegradable ring 400 can have different degradation properties. For example, the rate of degradation (i.e., the rate at which a substance degrades) of biodegradable ring 400 may optionally be controlled in order to balance (i.e., maintain an equilibrium) the rate of degradation and the rate of drug release in order to obtain maximum inhibition of the fibrosis process development. Therefore, biodegradable ring 400 optionally and preferably remains functional for a specific period of time post implantation. Without wishing to be limited to a closed list, the rate of degradation of biodegradable ring 400 is dependent upon the material from which biodegradable ring 400 is composed, external factors such as those concerning the surrounding eye surface, as well as the interaction between the material of biodegradable ring 400 and the surrounding eye surface. For example, if biodegradable ring 400 is composed substantially of biodegradable hydrogels or hydrophilic polymers, then the swelling property of these materials, being in contact with the surrounding eye tissue is taken into consideration since it may influence the rate of degradation.

Without wishing to be limited by a closed list, there are various approaches which may optionally be employed by the disclosed invention to obtain the appropriate material to be utilized by biodegradable ring 400 with the desired degradation properties. One approach concerns blending different polymers having different biodegradation and hydrophilic properties. For example, a biodegradable polymer exhibiting hydrophobic properties may optionally be blended with another biodegradable polymer exhibiting hydrophilic properties. Such a resultant blend would, on the one hand, substantially preserve certain control over the degradation process owing to the prevalence of the hydrophobic property, while, on the other hand, substantially attain the required water absorption owing to the prevalence of the hydrophilic property of the respective biodegradable polymer. Another approach involves utilizing co-polymers having particular segments having the desired physical as well as chemical properties. For example, the physicochemical properties of the polymer that is employed in biodegradable ring may optionally be altered in order to regulate the rate of biodegradation to match the release profile of active material needed for maximum inhibition of fibrosis process. Alternatively, other parameters may optionally be modified in order to change the degradation properties to substantially coincide with the maximum inhibition of fibrosis process. For example, the crystallinity (i.e., the degree of structural order), the stereoregularity (i.e., relating to the stereochemical regularity in the repeating units of the polymeric structure), the molecular weight, and the chemical structure of the material composing biodegradable ring may optionally be modified too.

EXAMPLE 1

Construction of Biodegradable Ring 400 and Loading with an Active Material

Materials:

1. Hydroxypropyl cellulose (HPC) with different molecular weights (different viscosity) supplied by Ashland (Hercules Incorporation-Aqualon Devision)-Biodegradable film forming Polymer Forth beneath are different grades of HPC which were used in the present study;

HPC LF-

HPC GF-

HPC MF-

| HPC Pharma Grade | Concentration in Water by Weight % | | |
|---|---|---|---|
| Viscosity Type | 2 | 5 | Molecular Weight |
| HPC LF- | | 75-150 | 95,000 |
| HPC GF- | 150-400 | | 370,000 |
| HPC MF | 4000-6500 | | 850,000 |

The data was taken from Hercules Incorporation-Klucel brochure (Physical and Chemical Properties)

2. Polyvinyl alcohol (PVA)—biodegradable film forming polymer

3. Tannic acid—cross-linker

4. Polysorbate 80 (Tween 80)—surface active agent—solubilizer

Methods:

In an initial experiment the solubility of the above polymers in phosphate buffer solution was tested. For this reason films of these polymers were prepared in water. The films were prepared by dissolving the polymer (3 grams) in purified water (97 gram) and pouring onto Teflon plate mold. The solution was then left on a flatted plane for at least 24 hours to finally attained a 250-500 micron thickness dried film. Pieces of resulting films 1 cm×1 cm were soaked in PBS at 37° C. and the integrity and dissolution of the film was followed by observation. The following is the duration of times, expressed by hours, which took for each polymer to dissolve under above conditions;

| Polymer Type | Dissolution time (hours) |
|---|---|
| HPC LF | 0.9 |
| HPC GF | 22.5 |
| HPC MF | 30.2 |
| PVA | 336 |

EXAMPLE 2

In further experiments in order to extend the duration of dissolution time, in other words to hinder the degradation of the ring, cross-linking of the above polymer took place. The cross linking was carried out by an in-situ reaction between the polymer and tannic acid which was used as a cross-linker. For this purpose film of different polymers including the cross-linker was prepared by dissolving the polymer in an organic solvent such as either ethanol or THF (tetrahydrofuran) together with the predetermined amount of tannic acid. The resulting solution was left to be dried for at least 24 hours to attained a dry film of the polymer and the cross-linker. The cross-linking reaction was carried out in-situ where the film was exposed to an aqueous solution. The cross-linking was used to hinder the dissolution of the polymer films.

Pieces of resulting films 1 cm×1 cm were soaked in PBS at 37° C. and the integrity and dissolution of the film was followed by observation. The following is the duration of times, expressed by days, which took for polymer films including different amounts of cross-linker to dissolve under above conditions;

The duration of times, expressed by days, which took for polymer films including different amounts of cross-linker to dissolve in PBS at 37° C.

| Polymer Type | Cross-linker content expressed by % w/w of the polymer | | |
|---|---|---|---|
| | 1% | 5% | 10% |
| HPC LF | 2 | 6.25 | 13 |
| HPC MF | 4 | 14 | 24 |
| PVA | 50 | NP | NP |

NP—not performed

EXAMPLE 3

In a further experiment the release profile of flurbiprofen (FBP) which is an NSAID (non-steroidal anti-inflammatory drugs) from cross-linked films in PBS at 37° C. was measured. For this purpose films based on HPC LF with different contents of the cross-linker were prepared.

The following is the composition of the films

1. HPC LF—film forming polymer

2. Polysorbate 80 surfactant/solubilizer

3. Tannic acid—Cross-linker

4. FBP—active material

Pieces of resulting films 1 cm×1 cm containing 5 mg FBP were soaked in PBS at 37° C. and release profile of the films was determined by measuring the dissolution of FBP during different period of times in PBS using an UV spectrophotometer and an appropriate calibration curve.

Figure 5:
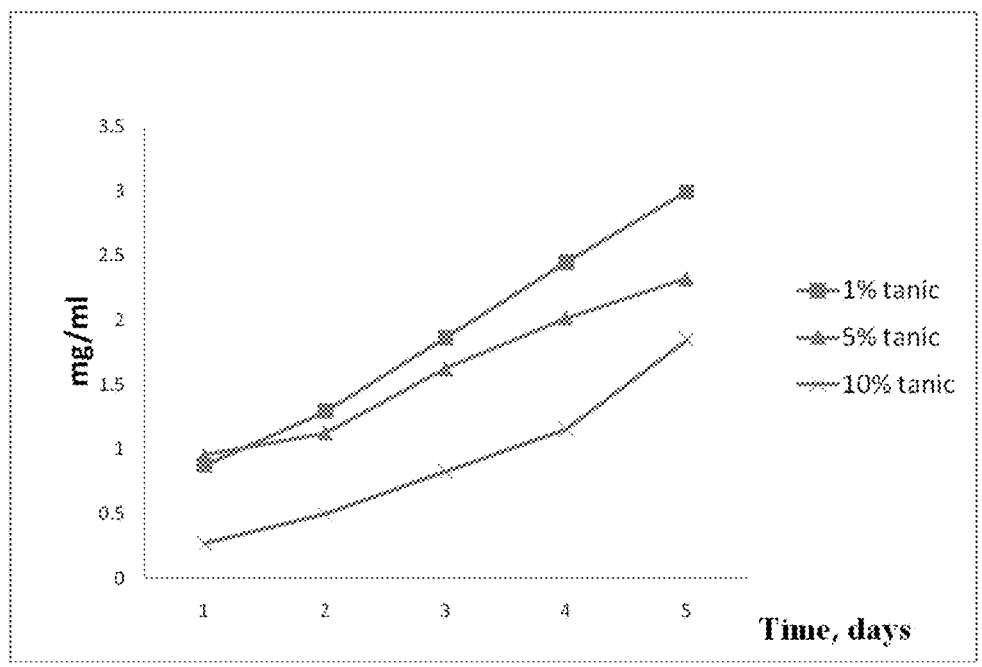
FIG. 5 illustrates a graph demonstrating the accumulative release profile of flurbiprofen (FBP) from films cross-linked by different cross-linker concentrations, according to some demonstrative embodiments described herein.

FIG. 5 which illustrates the accumulative release profile of flurbiprofen (FBP) from films cross-linked by different cross-linker (tannic acid) concentrations. FIG. 5 demonstrates the release rate of the active material in PBS, expressed by days, which took for polymer films including different amounts of cross-linker to dissolve under above conditions. The results demonstrated in FIG. 5 show that a controlled release from cross-linked polymer can be achieved where the release profile can be controlled by the cross-linking degree, i.e., the cross-linker (tannic acid) amount in the formulation.

It will be appreciated by persons skilled in the art that the disclosed invention is not limited to what has been particularly shown and described hereinabove. Rather the scope of the disclosed invention is defined only by the claims, which follow. Furthermore, any of the different embodiments and subembodiments described herein may be combined in different combinations, even if not explicitly disclosed herein.

The invention claimed is:

1. An ocular implant for regulating intraocular fluid pressure of an intraocular fluid contained within an anterior chamber of an eye of an implantee, the ocular implant comprising:
   a shunt having at least one inlet, and at least one outlet defining at least one respective shunt conduit there between, said at least one outlet communicating with a space, external to said anterior chamber; and
   at least one fluid absorbing conduit having a varying inner diameter adapted to drain said intraocular fluid and wherein said conduit is coupled with said at least one inlet, wherein said conduit comprises a material having a property of expanding when absorbing said intraocular fluid and contracting when desorbing from said intraocular fluid;
   wherein said conduit is adapted to be in at least one of two states:
      a first state wherein said material is expanded and said conduit has a first inner diameter and a first rate of intraocular fluid drainage; and
      a second state herein said material is contracted and said conduit has a second inner diameter and a second rate of intraocular fluid drainage; and
   wherein the first inner diameter is greater than the second inner diameter and said first rate of intraocular fluid drainage is greater than second rate of intraocular fluid drainage.

2. The ocular implant according to claim 1, wherein at least a portion of said shunt is substantially tubular, said at least one fluid absorbing conduit is substantially in the form of a generally truncated hollow cone of variable thickness, having a proximal end and an apical end defining a length of said at least one fluid absorbing conduit there between, wherein said proximal end is coupled circumferentially with said at least one inlet.

3. The ocular implant according to claim 1, further comprising an elastomer, which at least partially circumferentially covers an outer surface of said at least one fluid absorbing conduit along at least a portion of said length, said elastomer resists the expansion of said at least one fluid absorbing conduit, when said at least one fluid absorbing conduit expands, and promotes the contraction of said at least one fluid absorbing conduit, when said fluid absorbing conduit contracts.

4. The ocular implant according to claim 2, further comprising an elastomer, which at least partially circumferentially covers an outer surface of said at least one fluid absorbing conduit along at least a portion of said length, said elastomer resists the expansion of said at least one fluid absorbing conduit, when said at least one fluid absorbing conduit expands, and promotes the contraction of said at least one fluid absorbing conduit, when said fluid absorbing conduit contracts.

5. The ocular implant according to claim 4, wherein said elastomer is further coupled with said shunt, said elastomer at least partially circumferentially covers an outer surface of said shunt.

6. The ocular implant according to claim 3, wherein said elastomer has a variable thickness when said elastomer is at an equilibrium state.

7. The ocular implant according to claim 4, wherein said elastomer couples between said shunt and said fluid absorbing conduit.

8. The ocular implant according to claim 7, wherein said shunt and said at least one fluid absorbing conduit are physically separated from each other.

9. The ocular implant according to claim 4, wherein said elastomer at least partially circumferentially covers at least one of an inner surface of said shunt and an inner surf ace of said at least one fluid absorbing conduit.

10. The ocular implant according to claim 4, wherein said at least one fluid absorbing conduit having a generally elongated shape, extends within said shunt conduit, at least partially along a shunt conduit length of said shunt conduit, at least a portion of said at least one fluid absorbing conduit protruding exteriorly from said shunt conduit, said elastomer at least partially circumferentially covering said at least a portion and said shunt, thereby coupling between said at least one fluid absorbing conduit and said shunt.

11. The ocular implant according to claim 10, wherein said intraocular fluid diffuses through said at least one fluid absorbing conduit from said at least a portion to said at least one outlet.

12. The ocular implant according to claim 10, wherein at least a portion of said elastomer circumferentially covers exteriorly said shunt.

13. The ocular implant according to claim 10, wherein at least a portion of said elastomer extends within said shunt conduit, at least partially along said shunt conduit length, at least partially circumferentially covering said at least one fluid absorbing conduit.

14. The ocular implant according claim 1, wherein said at least one fluid absorbing conduit is coupled with said shunt, within said shunt conduit, wherein a shunt conduit length of said shunt conduit is substantially greater than a dimension of said at least one fluid absorbing conduit that is substantially parallel to said shunt conduit length.

15. The ocular implant according to claim 1, wherein at least a portion of said ocular implant is of a generally arrow shape, said generally arrow shape having a tip portion and a shaft portion, said tip portion being of a generally hollow frusto-conical shape having a base and an apex, said base having a base opening, said apex having a substantially central apex opening, said shaft portion being of a generally tubular shape, said shaft portion coupled substantially perpendicularly to said base, coaxially with said base opening.

16. The ocular implant according to claim 15, wherein said substantially tip portion incorporates a sharp angled leading edge.

17. The ocular implant according to claim 15, wherein said shaft portion corresponds with said shunt, and said tip portion corresponds with said at least one fluid absorbing conduit.

18. The ocular implant according to claim 15, wherein said shaft portion partially extends into a hollow region of said tip portion.

19. The ocular implant according to claim 15, wherein said tip portion further includes a front tubular extension coupled circumferentially therewith at said apex opening.

20. The ocular implant according to claim 19, wherein said front tubular extension corresponds with said at least one fluid absorbing conduit.

21. An ocular implant for regulating intraocular fluid pressure of an intraocular fluid contained within an anterior chamber of an eye of an implantee, the ocular implant comprising:
- a shunt having at least one inlet, and at least one outlet defining at least one respective shunt conduit there between, said at least one outlet communicating with a space, external to said anterior chamber;
- at least one fluid absorbing conduit coupled with said at least one inlet, said fluid absorbing conduit composed from a material having a property of expanding when absorbing said intraocular fluid and contracting when desorbing from said intraocular fluid, said at least one fluid absorbing conduit having at least one port, said at least one fluid absorbing conduit coupled with said shunt, and communicating with said intraocular fluid, said at least one port increasing, when absorption of said intraocular fluid by said fluid absorbing conduit increases, and said at least one port decreasing, when desorption of said intraocular fluid by said fluid absorbing conduit increases;
- wherein at least a portion of said shunt is substantially tubular, said at least one fluid absorbing conduit is substantially in the form of a generally truncated hollow cone of variable thickness, having a proximal end and an apical end defining a length of said at least one fluid absorbing conduit there between, wherein said proximal end is coupled circumferentially with said at least one inlet; and
- wherein said at least one fluid absorbing conduit further comprising an elastomer, which at least partially circumferentially covers an outer surface of said at least one fluid absorbing conduit along at least a portion of said length, said elastomer resists the expansion of said at least one fluid absorbing conduit, when said at least one fluid absorbing conduit expands, and promotes the contraction of said at least one fluid absorbing conduit, when said fluid absorbing conduit contracts.

* * * * *